US010710985B2

(12) United States Patent
Gaufreteau et al.

(10) Patent No.: US 10,710,985 B2
(45) Date of Patent: Jul. 14, 2020

(54) INDOLIN-2-ONE DERIVATIVES

(71) Applicant: Hoffmann-La Roche Inc., Little Falls, NJ (US)

(72) Inventors: Delphine Gaufreteau, Kembs (FR); Sabine Kolczewski, Loerrach (DE); Jean-Marc Plancher, Hagenthal-la-Bas (FR); Theodor Stoll, Binningen (CH); Remy Halm, Lutter (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/971,323

(22) Filed: May 4, 2018

(65) Prior Publication Data

US 2018/0251449 A1 Sep. 6, 2018

Related U.S. Application Data

(63) Continuation of application No. PCT/EP2016/076332, filed on Nov. 2, 2016.

(30) Foreign Application Priority Data

Nov. 6, 2015 (EP) .................................... 15193342

(51) Int. Cl.

| | |
|---|---|
| ***C07D 403/14*** | (2006.01) |
| ***C07D 401/14*** | (2006.01) |
| ***C07D 471/04*** | (2006.01) |
| ***A61K 31/506*** | (2006.01) |
| ***A61P 25/32*** | (2006.01) |
| ***A61P 25/36*** | (2006.01) |
| ***A61P 25/28*** | (2006.01) |
| ***A61P 25/18*** | (2006.01) |
| ***A61P 25/22*** | (2006.01) |
| ***A61P 25/24*** | (2006.01) |
| ***A61P 25/08*** | (2006.01) |
| ***A61P 25/16*** | (2006.01) |
| *A61K 45/06* | (2006.01) |

(52) U.S. Cl.

CPC .......... *C07D 403/14* (2013.01); *A61K 31/506* (2013.01); *A61P 25/08* (2018.01); *A61P 25/16* (2018.01); *A61P 25/18* (2018.01); *A61P 25/22* (2018.01); *A61P 25/24* (2018.01); *A61P 25/28* (2018.01); *A61P 25/32* (2018.01); *A61P 25/36* (2018.01); *C07D 401/14* (2013.01); *C07D 471/04* (2013.01); *A61K 45/06* (2013.01); *A61K 2300/00* (2013.01)

(58) Field of Classification Search

None

See application file for complete search history.

(56) References Cited

U.S. PATENT DOCUMENTS

| | | | |
|---|---|---|---|
| 6,090,818 | A | 7/2000 | Foulon et al. |
| 8,946,282 | B2 | 2/2015 | Chern et al. |
| 9,616,053 | B2 | 4/2017 | Brunner et al. |
| 2006/0253263 | A1 | 11/2006 | Meshkin |
| 2008/0039496 | A1 | 2/2008 | Blackburn et al. |
| 2011/0053936 | A1 | 3/2011 | Eastwood et al. |
| 2016/0095844 | A1 | 4/2016 | Brunner et al. |
| 2017/0101409 | A1 | 4/2017 | Hilpert et al. |
| 2018/0251449 | A1 | 9/2018 | Gaufreteau et al. |

(Continued)

FOREIGN PATENT DOCUMENTS

| | | |
|---|---|---|
| CA | 2196809 | 7/1995 |
| EP | 2895476 | 6/2016 |

(Continued)

OTHER PUBLICATIONS (ISR and Written Opinion of PCT/EP2015/064016 (dated Aug. 4, 2015))

(Continued)

*Primary Examiner* — Po-Chih Chen

(74) *Attorney, Agent, or Firm* — Todd M. Crissey

(57) ABSTRACT

The present invention is concerned with indolin-2-one derivatives of general formula

I

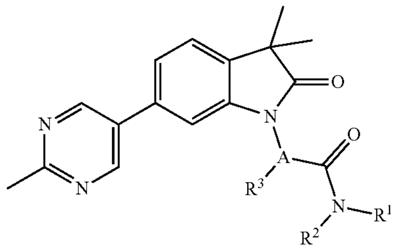

wherein the substituents are defined in claim 1.

The compounds may be used in the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, effects in arthritis, autoimmune disease, viral and fungal infections, cardiovascular diseases, ophthalmology and inflammatory retinal diseases and balance problems, epilepsy and neurodevelopmental disorders with co-morbid epilepsy.

34 Claims, No Drawings

(56) References Cited

U.S. PATENT DOCUMENTS

| | | | |
|---|---|---|---|
| 2018/0251450 A1 | 9/2018 | Gaufreteau et al. | |
| 2018/0251451 A1 | 9/2018 | Gaufreteau et al. | |
| 2018/0251455 A1 | 9/2018 | Gaufreteau et al. | |

FOREIGN PATENT DOCUMENTS

| | | | |
|---|---|---|---|
| JP | 10-503503 | | 3/1998 |
| JP | 2004-501192 | A | 1/2004 |
| JP | 2008-536941 | A | 9/2008 |
| JP | 2009-541493 | | 11/2009 |
| TW | 201504223 | A | 2/2015 |
| WO | 91/06545 | A1 | 5/1991 |
| WO | 94/10171 | | 5/1994 |
| WO | 96/04272 | | 2/1996 |
| WO | 98/25901 | A1 | 6/1998 |
| WO | 00/40581 | | 7/2000 |
| WO | 01/74775 | | 10/2001 |
| WO | 2001/72708 | | 10/2001 |
| WO | 02/00217 | A1 | 1/2002 |
| WO | 2004/060902 | A2 | 7/2004 |
| WO | 2005/108388 | A1 | 11/2005 |
| WO | 2006/113864 | A2 | 10/2006 |
| WO | 2006/113875 | A2 | 10/2006 |
| WO | 2007/006677 | A1 | 1/2007 |
| WO | 2008/002946 | A2 | 1/2008 |
| WO | 2008/046083 | A2 | 4/2008 |
| WO | 2008/080842 | | 7/2008 |
| WO | 2008/080970 | A1 | 7/2008 |
| WO | 2008/080973 | | 7/2008 |
| WO | 2009/124692 | A1 | 10/2009 |
| WO | 2009/132774 | A1 | 11/2009 |
| WO | 2010/066684 | A2 | 6/2010 |
| WO | 2014/040969 | A1 | 3/2014 |
| WO | 2014/202493 | A1 | 12/2014 |
| WO | 2015/197567 | | 12/2015 |
| WO | 2016/160755 | | 10/2016 |
| WO | 2017/076842 | | 5/2017 |
| WO | 2017/076852 | | 5/2017 |
| WO | 2017/076931 | | 5/2017 |
| WO | 2017/076932 | | 5/2017 |
| WO | 2017/079641 | | 5/2017 |
| WO | 2017/079759 | | 5/2017 |

OTHER PUBLICATIONS

Anne E. King et al., "Nucleoside transporters: from scavengers to novel therapeutic targets" Trends in Pharmacological Science 27(8):416-425 ( 2006).

Daniela Alberati et al., "Pharmacological evaluation of a novel assay for detecting glycine transporter 1 inhibitors and their antipsychotic potential" Pharmacology, Biochemistry and Behavior 97:185-191 ( 2010).

Elena P. Calandre et al., "The Role of Antipsychotics in the Management of Fibromyalgia" CNS Drugs 26(2): 135-153 ( 2012)

Gregory I Liou et al., "Diabetic retinopathy: Role of inflammation and potential therapies for anti-inflammation" World Journal of Diabetes 1(1):12-18 (Mar. 15, 2010).

ISR and Written Opinion of PCT/EP2016/076332 (dated Dec. 8, 2016).

ISR and Written Opinion of PCT/EP2016/076472 (dated Dec. 12, 2016).

ISR and PCT/EP2016/076315 (dated Jan. 4, 2017).

ISR of PCT/EP2016/076473 (dated Dec. 21, 2016).

Mashkovskiy, "Novaya Volna" Drugs 1:11 ( 2001).

INDOLIN-2-ONE DERIVATIVES

The present invention is concerned with indolin-2-one derivatives of general formula

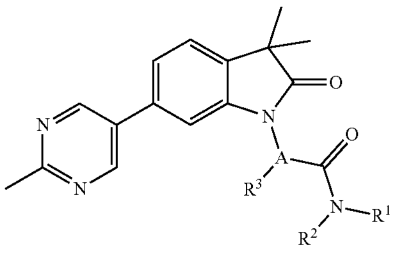

I wherein

A is phenyl or a five or six membered heteroaryl group, containing one or two N atoms, selected from

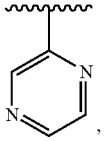, 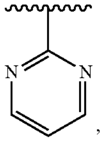, 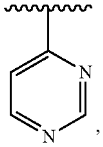, 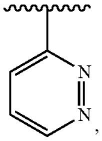,

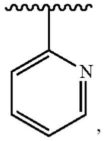, 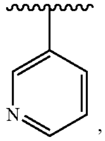, 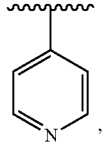, or 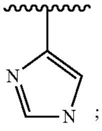;

or the amide group —C(O)—$NR^1R^2$ may form together with two neighboring carbon atoms from the group A an additional fused ring, selected from

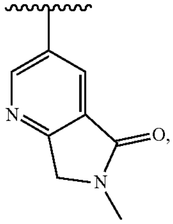, 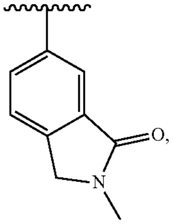, or

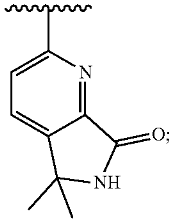;

$R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen; or $R^1$ and $R^2$ may form together with the N atom to which they are attached the group

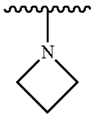

$R^3$ is hydrogen or lower alkyl;

as well as with a pharmaceutically acceptable salt thereof, with a racemic mixture, or with its corresponding enantiomer and/or optical isomer and/or stereoisomer thereof.

The amide group $C(O)NR^1R^2$ and $R^3$ may have different positions on A.

Now it has been found that the compounds of formula I may be used for the treatment of CNS diseases. The described compounds have been shown to reverse the L-687,414 ((3R,4R)-3 amino-1-hydroxy-4-methyl-pyrrolidin-2-one, a NMDA glycine site antagonist) induced hyperlocomotion, a behavioral pharmacodynamic mouse model for schizophrenia, described by D. Alberati et al. in *Pharmacology, Biochemistry and Behavior,* 97 (2010), 185-191. The authors described that hyperlocomotion induced by L-687,414 was inhibited by a series of known antipsychotic drugs. The compounds of formula I demonstrate marked activity in this model. These findings predict antipsychotic activity for the present compounds, making them useful for the treatment of positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems, epilepsy and neurodevelopmental disorders with co-morbid epilepsy.

In addition to the reversal of L-687,414 induced hyperlocomotion experiment as described above, some compounds of the present invention have been tested in SmartCube®, an automated system in which the behaviors of compound-treated mice in response to multiple challenges are captured by digital video and analyzed with computer algorithms (Roberds et al., *Frontiers in Neuroscience,* 2011, Vol. 5, Art. 103, 1-4; Vadim Alexandrov, Dani Brunner, Taleen Hanania, Emer Leahy *Eur. J Pharmacol.* 2015, 750, 82-99). In this way, the neuro-pharmacological effects of a test compound can be predicted by similarity to major classes of compounds, such as antipsychotics, anxiolytics and antidepressants. Examples 2, 7, 11, 16, 24 and 29 show similarity to atypical antipsychotics. The results are shown in Table 3.

In addition to the above-mentioned experiments, it has been shown that some of the compounds of formula I are also ENT1 inhibitors (equilibrative nucleoside transporter 1 protein). Therapeutic potential of ENT1 inhibitors is directly or indirectly (via effects of adenosine and/or adenosine receptor modulation) described in the literature for the treatment of the following diseases:

autoimmune disease (US 2006/253263), cancer (WO9857643), viral infections and fungal infections (WO2004060902), neurodegenerative disease, Parkinson's disease, Alzheimer's disease, Huntington's disease, amyotrophic lateral sclerosis, psychiatric diseases, substance abuse, ADHD, depression, epilepsy, anxiety, schizophrenia (WO0168105, EP 1252910, EP1612210, WO2009018275), autism spectrum disorders (Susan A. Masinoa, Masahito Kawamura Jr., Jessica L. Cotea, Rebecca B. Williams, David N. Ruskina, *Neuropharmacology,* 2013, 68, 116-121., pain (WO2009062990, WO2009064497), inflammation, asthma, (US 2007213296, *Inflammation research,* 2011, 60, 75-76), cardiovascular diseases (*Trends in Pharmacological science,* 2006, 27, 416-425), sleep disorders, (*Psychopharmacology,* 1987, 91, 434-439), ophthalmology and inflammatory retinal diseases (*World Journal of Diabetes*, vol. 1, 12-18), epilepsy and neurodevelopmental disorders with co-morbid epilepsy (*ENT*1 *Inhibition Attenuates Epileptic Seizure Severity Via Regulation of Glutamatergic Neurotransmission,* Xu et al, *Neuromol Med* (2015) 17:1-11 and *Epigenetic changes induced by adenosine augmentation therapy prevent epileptogenesis*, Williams-Karnesky et al *J Clin Invest.* 2013 August; 123(8):3552-63.

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone and olanzapine, however, fail to significantly ameliorate the negative symptoms and cognitive dysfunction.

Antipsychotic drugs have shown clinical efficacy for the treatment of the following diseases:

Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs,* 2012, 26, 2, 135-53).

Schizoaffective disorders: includes psychotic and affective symptoms, this disorder falls on a spectrum between bipolar disorders (with depressive and manic episodes, alcohol and drug addiction, substance abuse) and schizophrenia. *J. Clin. Psychiatry,* 2010, 71, S2, 14-9, *Pediatr. Drugs* 2011, 13, 5, 291-302

Major depression: *BMC Psychiatry* 2011, 11, 86

Treatment resistent depression: *Journal of Psychopharmacology,* 0(0) 1-16

Anxiety: *European Neuropsychopharmacology,* 2011, 21, 429-449

Bipolar disorders: *Encephale, International J. of Neuropsychopharmacology,* 2011, 14, 1029-104, *International J. of Neuropsychopharmacology,* 2012, 1-12; *J. of Neuropsychopharmacology,* 2011, 0, 0, 1-15

Mood disorders: *J. Psychopharmacol.* 2012, January 11, *CNS Drugs,* 2010, 2, 131-61

Autism: *Current opinion in pediatrics,* 2011, 23, 621-627*; J. Clin. Psychiatry,* 2011, 72, 9, 1270-1276

Alzheimer's disease: *J. Clin. Psychiatry,* 2012, 73, 1, 121-128

Parkinson's disease: *Movement Disorders,* 2011, 26, 6

Chronic fatigue syndrome: *European Neuropsychopharmacology,* 2011, 21, 282-286

Borderline Personality disorder: *J. Clin. Psychiatry,* 2011, 72, 10, 1363-1365 *J. Clin. Psychiatry,* 2011, 72, 10, 1353-1362

Anti-inflammatory effects in arthritis: *European J. of Pharmacology,* 2012, 678, 55-60

Objects of the present invention are novel compounds of formula I and the use of compounds of formula I and their pharmaceutically acceptable salts for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, arthritis, autoimmune disease, viral and fungal infections, cardiovascular diseases, ophthalmology and inflammatory retinal diseases and balance problems, epilepsy and neurodevelopmental disorders with co-morbid epilepsy.

Further objects of the present invention are medicaments containing such novel compounds as well as methods for preparation of compounds of formula I, a combination of compounds of formula I with marketed antipsychotics, antidepressants, anxiolytics or mood stabilizers, and methods for the treatment of CNS disorders as mentioned above.

Encompassed by the present invention are corresponding prodrugs of compounds of formula I.

A common antipsychotic drug for the treatment of schizophrenia is olanzapine. Olanzapine (Zyprexa) belongs to a drug class known as atypical antipsychotics. Other members of this class include for example clozapine (Clozaril), risperidone (Risperdal), aripiprazole (Abilify) and ziprasidone (Geodon).

Olanzapine is approved for the treatment of psychotic disorders, long term treatment of bipolar disorders and in combination with fluoxetine for the treatment of depressive episodes associated with bipolar disorders and for the treatment of resistant depression. The compounds of the present invention may be combined with antipsychotic drugs like olanzapine (Zyprexa), clozapine (Clozaril), risperidone (Risperdal), aripiprazole (Abilify), amisulpride (Solian), asenapine (Saphris), blonanserin (Lonasen), clotiapine (Entumine), iloperidone (Fanapt), lurasidone (Latuda), mosapramine (Cremin), paliperidone (Invega), perospirone (Lullan), quetiapine (Seroquel), remoxipride (Roxiam), sertindole (Serdolect), sulpiride (Sulpirid, Eglonyl), ziprasidone (Geodon, Zeldox), zotepine (Nipolept), haloperidol (Haldol, Serenace), droperidol (Droleptan), chlorpromazine (Thorazine, Largactil), fluphenazine (Prolixin), perphenazine (Trilafon), prochlorperazine (Compazine), thioridazine (Mellaril, Melleril), trifluoperazine (Stelazine), triflupromazine (Vesprin), levomepromazine (Nozinan), promethazine (Phenergan), pimozide (Orap) and cyamemazine (Tercian).

One preferred embodiment of the invention is a combination, wherein the marketed antipsychotic drug is olanzapine (Zyprexa), clozapine (Clozaril), risperidone (Risperdal), aripiprazole (Abilify) or ziprasidone.

Furthermore, the compounds of the present invention can be combined with antidepressants such as selective serotonin reuptake inhibitors [Citalopram (Celexa), Escitalopram (Lexapro, Cipralex), Paroxetine (Paxil, Seroxat), Fluoxetine (Prozac), Fluvoxamine (Luvox), Sertraline (Zoloft, Lustral)], serotonin-norepinephrine reuptake inhibitors [Duloxetine (Cymbalta), Milnacipran (Ixel, Savella), Venlafaxine (Effexor), Desvenlafaxine (Pristiq), Tramadol (Tramal, Ultram), Sibutramine (Meridia, Reductil)], serotonin antagonist and reuptake inhibitors [Etoperidone (Axiomin, Etonin), Lubazodone (YM-992, YM-35,995), Nefazodone (Serzone, Nefadar), Trazodone (Desyrel)], norepinephrine reuptake inhibitors [Reboxetine (Edronax), Viloxazine (Vivalan), Atomoxetine (Strattera)], norepinephrine-dopamine reuptake inhibitors [Bupropion (Wellbutrin, Zyban), Dexmethylphenidate (Focalin), Methylphenidate (Ritalin, Concerta)], norepinephrine-dopamine releasing agents [Amphetamine (Adderall), Dextroamphetamine (Dexedrine), Dextromethamphetamine (Desoxyn), Li sdexamfetamine (Vyvanse)], tricyclic antidepressants [Amitriptyline (Elavil, Endep), Clomipramine (Anafranil), Desipramine (Norpramin, Pertofrane), Dosulepin [Dothiepin] (Prothiaden), Doxepin (Adapin, Sinequan), Imipramine (Tofranil), Lofepramine (Feprapax, Gamanil, Lomont), Nortriptyline (Pamelor), Protriptyline (Vivactil), Trimipramine (Surmontil)], tetracyclic antidepressants [Amoxapine (Asendin), Maprotiline (Ludiomil), Mianserin (Bolvidon, Norval, Tolvon), Mirtazapine (Remeron)], monoamine oxidase inhibitors [Isocarboxazid (Marplan), Moclobemide (Aurorix, Manerix), Phenelzine (Nardil), Selegiline [L-Deprenyl] (Eldepryl, Zelapar, Emsam), Tranylcypromine (Parnate), Pirlindole (Pirazidol)], 5-HT1A Receptor Agonists [Buspirone (Buspar), Tandospirone (Sediel), Vilazodone (Viibryd)], 5-HT2 Receptor Antagonists [Agomelatine (Valdoxan), Nefazodone (Nefadar, Serzone), selective Serotonin Reuptake Enhancers [Tianeptine].

A preferred embodiment of this invention is a combination, wherein the marketed anti-depressive drug is citalopram (Celexa), escitalopram (Lexapro, Cipralex), paroxetine (Paxil, Seroxat), fluoxetine (Prozac), sertraline (Zoloft, Lustral) duloxetine (Cymbalta), milnacipran (Ixel, Savella), venlafaxine (Effexor), or mirtazapine (Remeron).

Compounds can also be combined with anxiolytics such as Alprazolam (Helex, Xanax, Xanor, Onax, Alprox, Restyl, Tafil, Paxal), Bretazenil, Bromazepam (Lectopam, Lexotanil, Lexotan, Bromam), Brotizolam (Lendormin, Dormex, Sintonal, Noctilan), Chlordiazepoxide (Librium, Risolid, Elenium), Cinolazepam (Gerodorm), Clonazepam (Rivotril, Klonopin, Iktorivil, Paxam), Clorazepate (Tranxene, Tranxilium), Clotiazepam (Veratran, Clozan, Rize), Cloxazolam (Sepazon, Olcadil), Delorazepam (Dadumir), Diazepam (Antenex, Apaurin, Apzepam, Apozepam, Hexalid, Pax, Stesolid, Stedon, Valium, Vival, Valaxona), Estazolam (ProSom), Etizolam (Etilaam, Pasaden, Depas), Flunitrazepam (Rohypnol, Fluscand, Flunipam, Ronal, Rohydorm), Flurazepam (Dalmadorm, Dalmane), Flutoprazepam (Restas), Halazepam (Paxipam), Ketazolam (Anxon), Loprazolam (Dormonoct), Lorazepam (Ativan, Temesta, Tavor, Lorabenz), Lormetazepam (Loramet, Noctamid, Pronoctan), Medazepam (Nobrium), Midazolam (Dormicum, Versed, Hypnovel, Dormonid), Nimetazepam (Erimin), Nitrazepam (Mogadon, Alodorm, Pacisyn, Dumolid, Nitrazadon), Nordazepam (Madar, Stilny), Oxazepam (Seresta, Serax, Serenid, Serepax, Sobril, Oxabenz, Oxapax), Phenazepam (Phenazepam), Pinazepam (Domar), Prazepam (Lysanxia, Centrax), Premazepam, Quazepam (Doral), Temazepam (Restoril, Normison, Euhypnos, Temaze, Tenox), Tetrazepam (Mylostan), Triazolam (Halcion, Rilamir), Clobazam (Frisium, Urbanol), Eszopiclone (Lunesta), Zaleplon (Sonata, Starnoc), Zolpidem (Ambien, Nytamel, Stilnoct, Stilnox, Zoldem, Zolnod), Zopiclone (Imovane, Rhovane, Ximovan; Zileze; Zimoclone; Zimovane; Zopitan; Zorclone), Pregabalin (Lyrica) and Gabapentin (Fanatrex, Gabarone, Gralise, Neurontin, Nupentin).

One preferred embodiment of the invention is a combination, wherein the marketed anxiolytic drug is alprazolam (Helex, Xanax, Xanor, Onax, Alprox, Restyl, Tafil, Paxal), chlordiazepoxide (Librium, Risolid, Elenium), clonazepam (Rivotril, Klonopin, Iktorivil, Paxam), diazepam (Antenex, Apaurin, Apzepam, Apozepam, Hexalid, Pax, Stesolid, Stedon, Valium, Vival, Valaxona), Estazolam (ProSom), eszopiclone (Lunesta), zaleplon (Sonata, Starnoc), zolpidem (Ambien, Nytamel, Stilnoct, Stilnox, Zoldem, Zolnod), pregabalin (Lyrica) or gabapentin (Fanatrex, Gabarone, Gralise, Neurontin, Nupentin).

A further object of the invention is a combination with mood stabilizers such as Carbamazepine (Tegretol), Lamotrigine (Lamictal), Lithium (Eskalith, Lithane, Lithobid), and Valproic Acid (Depakote).

Compounds can also be combined with procognitive compounds such as donepezil (Aricept), galantamine (Razadyne), rivastigmine (Exelon) and memantine (Namenda).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, wherein the alkyl residue is attached via an oxygen atom.

As used herein, the term "lower alkyl substituted by hydroxy" denotes a group wherein the alkyl residue is as defined above, wherein at least one hydrogen atom is replaced by a hydroxy group.

As used herein, the term "lower alkyl substituted by halogen" denotes a group wherein the alkyl residue is as defined above, wherein at least one hydrogen atom is replaced by a halogen atom.

The term "cycloalkyl" denotes an alkyl ring with 3-6 carbon ring atoms.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula IA

IA

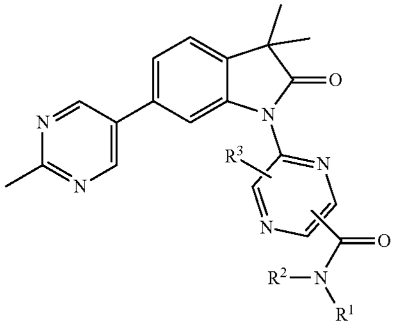

wherein $R^1/R^2$ are independently from each other hydrogen, lower alkyl, lower alkyl substituted by halogen, lower alkyl substituted by hydroxy, $—(CH_2)_2$-lower alkoxy, oxetanyl, cycloalkyl, $CH_2$-cycloalkyl, which cycloalkyl rings are optionally substituted by halogen; or $R^1$ and $R^2$ may form together with the N atom to which they are attach the group

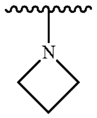

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 6-(3,3-dimethyl-6-(2-methylpyrimidin-5-yl)-2-oxoindolin-1-yl)-N,N-dimethylpyrazine-2-carboxamide 6-(3,3-dimethyl-6-(2-methylpyrimidin-5-yl)-2-oxoindolin-1-yl)-N-methylpyrazine-2-carboxamide 1-(6-(azetidine-1-carbonyl)pyrazin-2-yl)-3,3-dimethyl-6-(2-methylpyrimidin-5-yl)indolin-2-one 6-(3,3-dimethyl-6-(2-methylpyrimidin-5-yl)-2-oxoindolin-1-yl)-N-methyl-N-(2,2,2-trifluoroethyl)pyrazine-2-carboxamide 6-(3,3-dimethyl-6-(2-methylpyrimidin-5-yl)-2-oxoindolin-1-yl)-N-(2-methoxyethyl)-N-methylpyrazine-2-carboxamide 6-(3,3-dimethyl-6-(2-methylpyrimidin-5-yl)-2-oxoindolin-1-yl)-N-(2-hydroxyethyl)pyrazine-2-carboxamide 6-(3,3-dimethyl-6-(2-methylpyrimidin-5-yl)-2-oxoindolin-1-yl)-N-(2-methoxyethyl)pyrazine-2-carboxamide 6-(3,3-dimethyl-6-(2-methylpyrimidin-5-yl)-2-oxoindolin-1-yl)-N-(2,2,2-trifluoroethyl)pyrazine-2-carboxamide 6-(3,3-dimethyl-6-(2-methylpyrimidin-5-yl)-2-oxoindolin-1-yl)-N-isopropylpyrazine-2-carboxamide 6-(3,3-dimethyl-6-(2-methylpyrimidin-5-yl)-2-oxoindolin-1-yl)pyrazine-2-carboxamide 5-[3,3-dimethyl-6-(2-methylpyrimidin-5-yl)-2-oxoindolin-1-yl]-dimethylpyrazine-2-carboxamide N-(tert-butyl)-5-(3,3-dimethyl-6-(2-methylpyrimidin-5-yl)-2-oxoindolin-1-yl)-N-methylpyrazine-2-carboxamide 1-(5-(azetidine-1-carbonyl)pyrazin-2-yl)-3,3-dimethyl-6-(2-methylpyrimidin-5-yl)indolin-2-one 5-(3,3-dimethyl-6-(2-methylpyrimidin-5-yl)-2-oxoindolin-1-yl)-N-(2-methoxyethyl)-N-methylpyrazine-2-carboxamide 5-(3,3-dimethyl-6-(2-methylpyrimidin-5-yl)-2-oxoindolin-1-yl)pyrazine-2-carboxamide N-cyclopropyl-6-(3,3-dimethyl-6-(2-methylpyrimidin-5-yl)-2-oxoindolin-1-yl)pyrazine-2-carboxamide N-(3,3-difluorocyclobutyl)-6-(3,3-dimethyl-6-(2-methylpyrimidin-5-yl)-2-oxoindolin-1-yl)pyrazine-2-carboxamide N-cyclobutyl-6-(3,3-dimethyl-6-(2-methylpyrimidin-5-yl)-2-oxoindolin-1-yl)pyrazine-2-carboxamide 6-(3,3-dimethyl-6-(2-methylpyrimidin-5-yl)-2-oxoindolin-1-yl)-N-(oxetan-3-yl)pyrazine-2-carboxamide or N-(tert-butyl)-6-(3,3-dimethyl-6-(2-methylpyrimidin-5-yl)-2-oxoindolin-1-yl)pyrazine-2-carboxamide.

A further embodiment of the invention are compounds of formula IB

IB

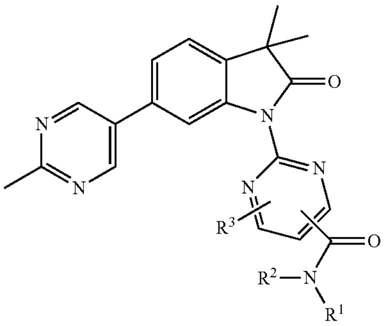

wherein $R^1/R^2$ are independently from each other hydrogen, lower alkyl, lower alkyl substituted by halogen, lower alkyl substituted by hydroxy, $—(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attach the group

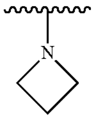 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 2-(3,3-dimethyl-6-(2-methylpyrimidin-5-yl)-2-oxoindolin-1-yl)-N-methylpyrimidine-4-carboxamide 2-(3,3-dimethyl-6-(2-methylpyrimidin-5-yl)-2-oxoindolin-1-yl)-N,N-dimethylpyrimidine-4-carboxamide or 2-(3,3-dimethyl-6-(2-methylpyrimidin-5-yl)-2-oxoindolin-1-yl)-N,5-dimethylpyrimidine-4-carboxamide.

A further embodiment of the invention are compounds of formula IC

IC

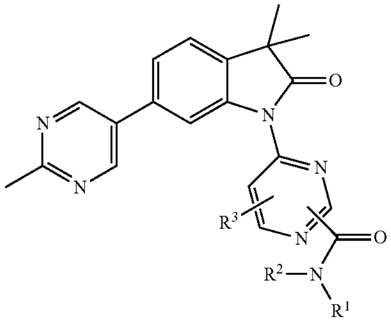

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

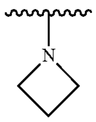 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 4-(3,3-dimethyl-6-(2-methylpyrimidin-5-yl)-2-oxoindolin-1-yl)-N,N-dimethylpyrimidine-2-carboxamide or 4-(3,3-dimethyl-6-(2-methylpyrimidin-5-yl)-2-oxoindolin-1-yl)-N-methylpyrimidine-2-carboxamide.

A further embodiment of the invention are compounds of formula ID

ID

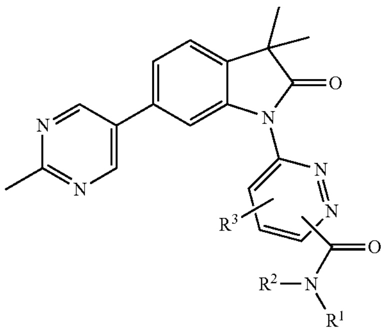

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

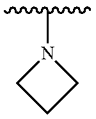

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compound 6-(3,3-dimethyl-6-(2-methylpyrimidin-5-yl)-2-oxoindolin-1-yl)-N,N-dimethylpyridazine-3-carboxamide.

A further embodiment of the invention are compounds of formula IE

IE

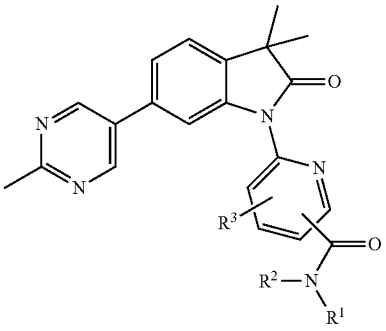

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

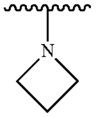 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 6-(3,3-dimethyl-6-(2-methylpyrimidin-5-yl)-2-oxoindolin-1-yl)-N-methylpicolinamide 6-(3,3-dimethyl-6-(2-methylpyrimidin-5-yl)-2-oxoindolin-1-yl)-N,N-dimethylpicolinamide N-cyclopropyl-6-(3,3-dimethyl-6-(2-methylpyrimidin-5-yl)-2-oxoindolin-1-yl)picolinamide N-(cyclopropylmethyl)-6-(3,3-dimethyl-6-(2-methylpyrimidin-5-yl)-2-oxoindolin-1-yl)picolinamide 6-(3,3-dimethyl-6-(2-methylpyrimidin-5-yl)-2-oxoindolin-1-yl)picolinamide 6-(3,3-dimethyl-6-(2-methylpyrimidin-5-yl)-2-oxoindolin-1-yl)-N,3-dimethylpicolinamide 6-(3,3-dimethyl-6-(2-methylpyrimidin-5-yl)-2-oxoindolin-1-yl)-N,N,3-trimethylpicolinamide or 6-(3,3-dimethyl-6-(2-methylpyrimidin-5-yl)-2-oxoindolin-1-yl)-N,N-dimethylnicotinamide.

A further embodiment of the invention are compounds of formula IF

IF

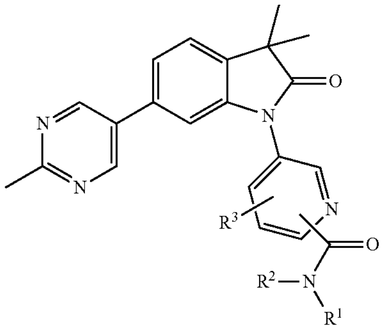

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

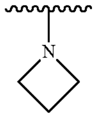 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 5-(3,3-dimethyl-6-(2-methylpyrimidin-5-yl)-2-oxoindolin-1-yl)-N,N-dimethylnicotinamide 1-(5-(azetidine-1-carbonyl)pyridin-3-yl)-3,3-dimethyl-6-(2-methylpyrimidin-5-yl)indolin-2-one 5-(3,3-dimethyl-6-(2-methylpyrimidin-5-yl)-2-oxoindolin-1-yl)-N-(2,2,2-trifluoroethyl)nicotinamide 5-(3,3-dimethyl-6-(2-methylpyrimidin-5-yl)-2-oxoindolin-1-yl)-N-methylnicotinamide or 5-(3,3-dimethyl-6-(2-methylpyrimidin-5-yl)-2-oxoindolin-1-yl)-N,2-dimethylnicotinamide.

A further embodiment of the invention are compounds of formula IG

IG

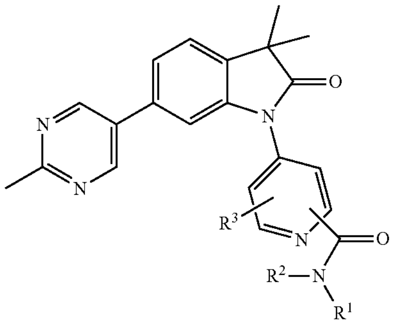

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

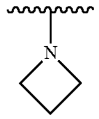 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 4-(3,3-dimethyl-6-(2-methylpyrimidin-5-yl)-2-oxoindolin-1-yl)-N,6-dimethylpicolinamide or 4-(3,3-dimethyl-6-(2-methylpyrimidin-5-yl)-2-oxoindolin-1-yl)-N-methylpicolinamide A further embodiment of the invention are compounds of formula IH

IH

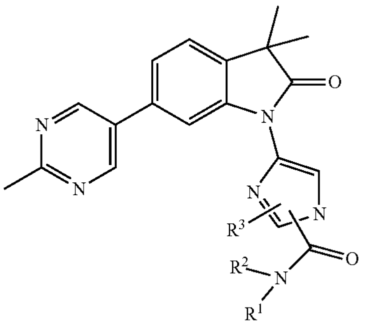

wherein $R^1/R^2$ are independently from each other hydrogen, lower alkyl, lower alkyl substituted by halogen, lower alkyl substituted by hydroxy, —$(CH_2)_2$-lower alkoxy, oxetanyl, cycloalkyl, $CH_2$-cycloalkyl, which cycloalkyl rings are optionally substituted by halogen;

or $R^1$ and $R^2$ may form together with the N atom to which they are attached the group

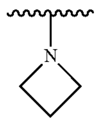 [SMILES: *N1CCC1]

$R^3$ is hydrogen or lower alkyl;

as well as with a pharmaceutically acceptable salt thereof, with a racemic mixture, or with its corresponding enantiomer and/or optical isomer and/or stereoisomer thereof, for example the compounds 4-(3,3-dimethyl-6-(2-methylpyrimidin-5-yl)-2-oxoindolin-1-yl)-N,1-dimethyl-1H-imidazole-2-carboxamide or 4-(3,3-dimethyl-6-(2-methylpyrimidin-5-yl)-2-oxoindolin-1-yl)-N,N,1-trimethyl-1H-imidazole-2-carboxamide.

A further embodiment of the invention are compounds of formula Ii wherein A is phenyl or a five or six membered heteroaryl group, containing one or two N atoms, and the amide group —C(O)—$NR^1R^2$ forms together with two neighboring carbon atoms from the group A an additional fused ring, which compounds are Ii-a

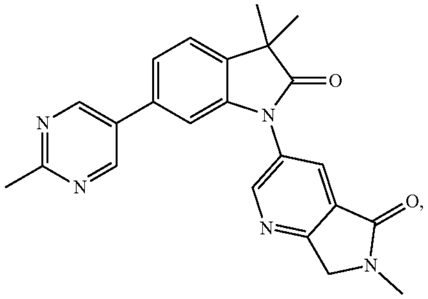

Ii-b

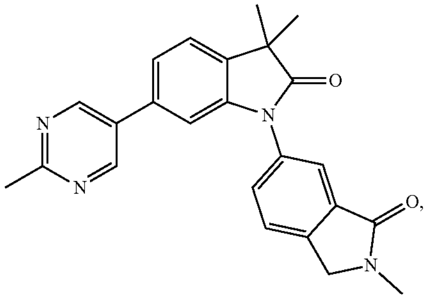

Ii-c

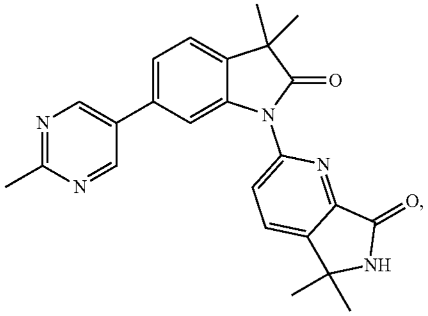

The present compounds of formula I and their pharmaceutically acceptable salts can be prepared by methods known in the art, for example, by processes described below, which processes comprise a) reacting a compound of formula

1

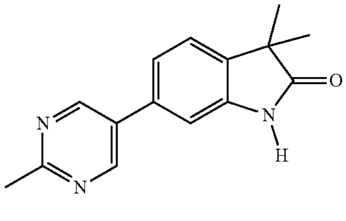

with a compound of formula

Y-A($R^3$)—C(O)—$NR^1R^2$ 2 to a compound of formula

I

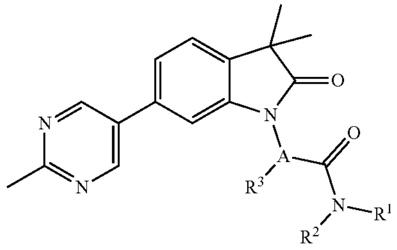

wherein Y is Cl, Br or I and the other groups have the meaning as described above and, if desired, converting the compounds obtained into pharmaceutically acceptable acid addition salts; or b) reacting a compound of formula

4

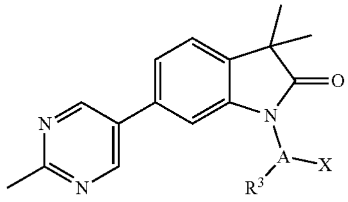

with $HNR^1R^2$ by aminocarbonylation in the presence of a ferrocene-palladium catalyst, with a source of carbon monoxide, preferencially Molybden-hexacarbonyl or with CO gas (50 bar) to a compound of formula

I

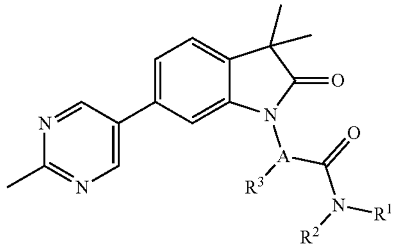

wherein X is Cl or Br and the other groups have the meaning as described above, and, if desired, converting the compounds obtained into pharmaceutically acceptable acid addition salts; or c) amidation of a compound of formula

6

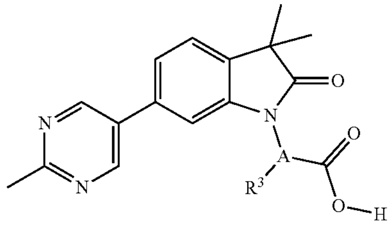

with $HNR^1R^2$ using an activating agent, preferred are HATU or TBTU, to give the compounds of formula I

I

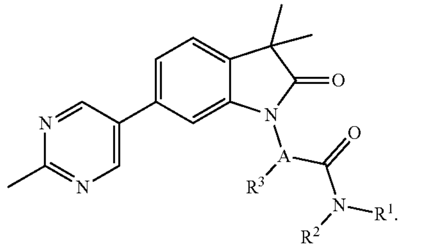

wherein the groups have the meaning as described above, and, if desired, converting the compounds obtained into pharmaceutically acceptable acid addition salts;

The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

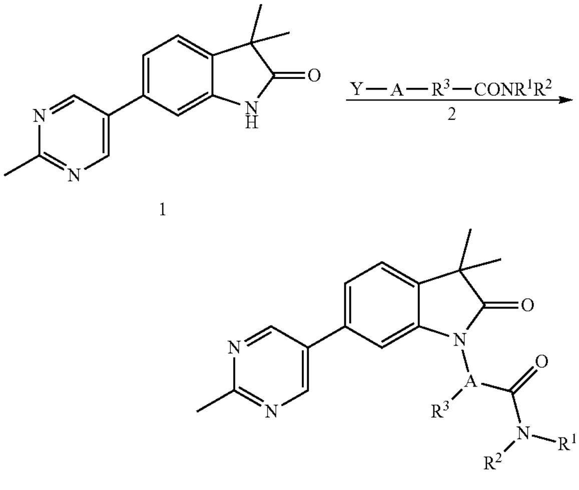

1

I

Compound of formula I with A=substituted pyrazines, pyrimidines, pyridazines, pyridines, imidazoles and fused rings can be prepared by coupling compounds 1 (WO2014/202493 A1) with aryl-halogenides 2 (Y═Cl, Br, I) in the presence of copper(I)iodide, a ligand such as N,N'-dimethylethylendiamine and a base, e.g. potassium carbonate.

Scheme 2

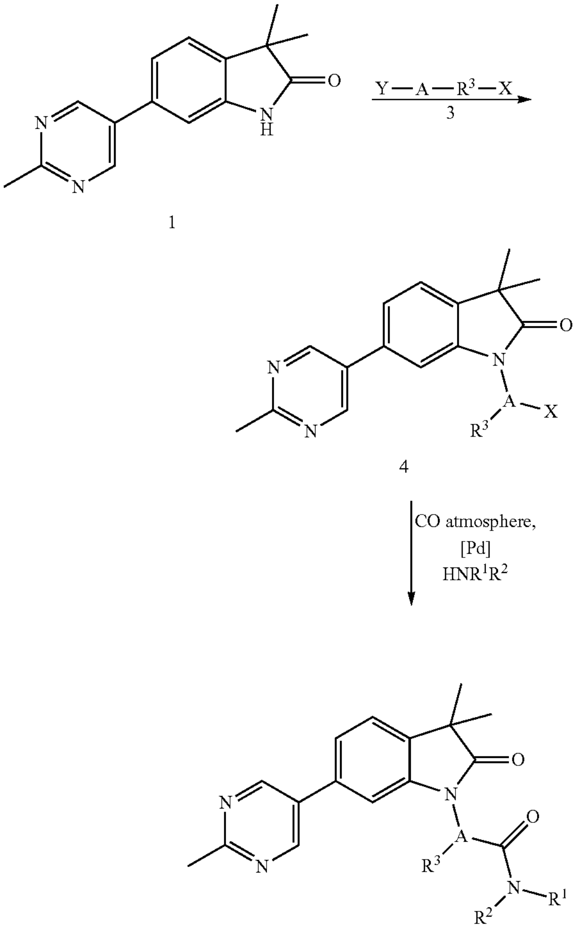

1

4

I

Compounds of formula 4 can be synthesized with compounds 1 (WO2014/202493 A1) and aryl-halogenides 3 (Y═Cl, Br, I) in the presence of copper(I)iodide, a ligand such as N,N'-dimethylethylendiamine and a base, e.g. potassium carbonate. Final compounds I can be prepared from compounds 4 (with X═Cl or Br) by aminocarbonylation in the presence of a ferrocene-palladium catalyst, with a source of carbon monoxide, preferencially Molybden-hexacarbonyl (0.3 eq) or with CO gas (50 bar).

Scheme 3

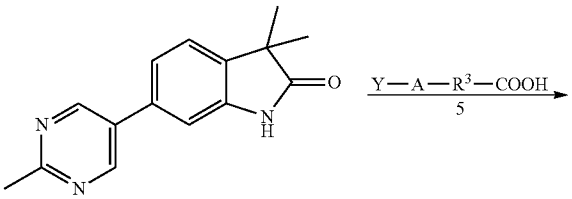

1

-continued

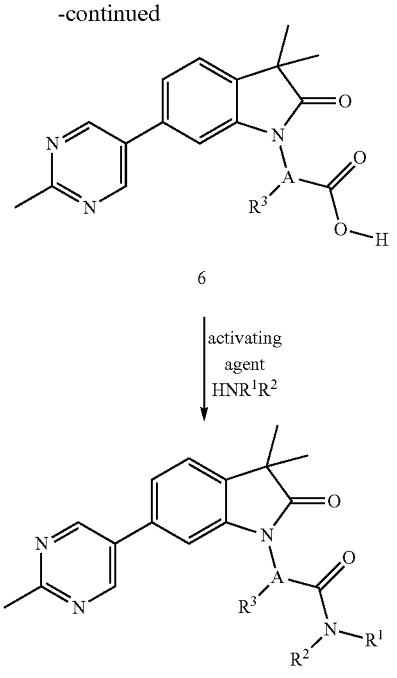

6

I

Compound of formula I can be prepared by coupling compounds 1 (WO2014/202493 A1) and acid-aryl-halogenides 5 (Y═Cl, Br, I) in the presence of a base, such as sodium hydride or potassium carbonate. Then amidation of compounds 6 was performed using an activating agent preferencially HATU or TBTU affording the targeted compounds I.

EXPERIMENTAL PART

The following examples are provided for illustration of the invention. They should not be considered as limiting the scope of the invention, but merely as being representative thereof.

Abbreviations

Boc, t-butyloxycarbonyl;
DIPEA, diisopropylethylamine;
DMAP, dimethylaminopyridine;
DMF, dimethylformamide;
DMSO, dimethylsulfoxide;
EDCI, 1-ethyl-3-(3-dimethylaminopropyl)carbodiimid;
EtOAc, ethyl acetate;
HATU, 1-[Bis(dimethylamino)methylene]-1H-1,2,3-triazolo[4,5-b]pyridinium 3-oxid hexafluorophosphate;
HOBt, 1-hydroxybenzotriazole;
MeOH, methanol;
NMP, N-methyl-2-pyrrolidon;
PMB, p-methoxybenzyl;
TBTU, O-(Benzotriazol-1-yl)-N,N,N',N'-tetramethyluronium tetrafluoroborate;
TFA, trifluoroacetic acid;
THF, tetrahydrofuran.
General:

Silica gel chromatography was either performed using cartridges packed with silica gel (ISOLUTE® Columns, TELOS™ Flash Columns) or silica-NH2 gel (TELOS™

Flash NH2 Columns) on ISCO Combi Flash Companion or on glass columns on silica gel 60 (32-60 mesh, 60 Å). MS: Mass spectra (MS) were measured with ion spray positive or negative method on a Perkin-Elmer SCIEX API 300.

Example 1

6-(3,3-Dimethyl-6-(2-methylpyrimidin-5-yl)-2-oxoindolin-1-yl)-N,N-dimethylpyrazine-2-carboxamide

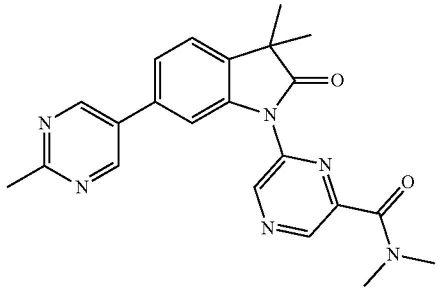

a) 1-(6-Bromopyrazin-2-yl)-3,3-dimethyl-6-(2-methylpyrimidin-5-yl)indolin-2-one

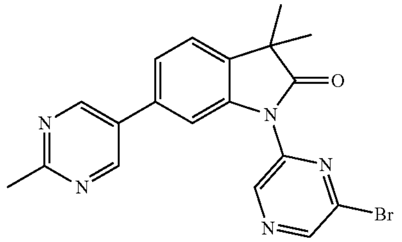 [SMILES: Cc1ncc(-c2ccc3c(c2)N(c2cncc(Br)n2)C(=O)C3(C)C)cn1]

3,3-Dimethyl-6-(2-methylpyrimidin-5-yl)indolin-2-one (1200 mg, 4.74 mmol, Eq: 1, WO2014/202493 A1), 2,6-dibromopyrazine (1.35 g, 568 μmol, Eq: 1.2), copper (I) iodide (90.2 mg, 474 μmol, Eq: 0.1), trans-N,N-dimethylcyclohexane 1,2-diamine (135 mg, 149 μl, 947 μmol, Eq: 0.2) and potassium carbonate (1.31 g, 9.47 mmol, Eq: 2) were dissolved in degassed 1,4-dioxane (15 ml) under inert atmosphere. The reaction mixture was heated to 100° C. and stirred for 16 h. The crude reaction mixture was cooled down then diluted with ethyl acetate and washed with saturated sodium bicarbonate. The organic phases were combined and washed with brine, dried over sodium sulfate then filtered and evaporated in vacuo.

The residue was purified by chromatography on silica gel to afford the desired product as a white solid (920 mg, 47%). MS (m/z)=412.1 [M+H]+ b) 6-(3,3-Dimethyl-6-(2-methylpyrimidin-5-yl)-2-oxoindolin-1-yl)-N,N-dimethylpyrazine-2-carboxamide

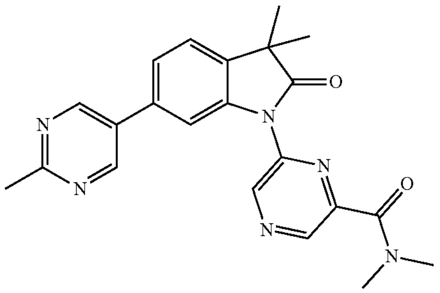

1-(6-Bromopyrazin-2-yl)-3,3-dimethyl-6-(2-methylpyrimidin-5-yl)indolin-2-one (140 mg, 341 Eq: 1), dimethylamine hydrochloride (41.7 mg, 512 μmol, Eq: 1.5), tributylamine (190 mg, 243 μl, 1.02 mmol, Eq: 3.00), tetraethylammonium chloride (10.6 mg, 64 μmol, Eq: 0.188) and olybden-hexacarbonyl (25.1 mg, 95.2 μmol, Eq: 0.279) were combined with diethylene glycol dimethyl ether (3 ml). The reaction mixture was heated to 150° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo.

The residue was purified by chromatography on silica gel to afford the desired product as a white solid (60 mg, 48%), MS (m/z)=403.3 [M+H]+

Example 2

6-(3,3-Dimethyl-6-(2-methylpyrimidin-5-yl)-2-oxoindolin-1-yl)-N-methylpyrazine-2-carboxamide

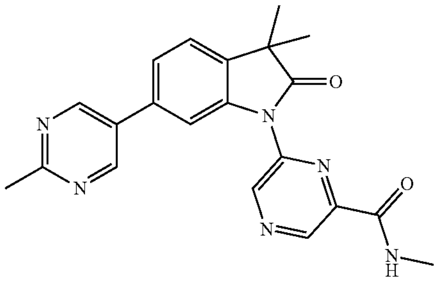

a) 1-(6-Chloropyrazin-2-yl)-3,3-dimethyl-6-(2-methylpyrimidin-5-yl)indolin-2-one

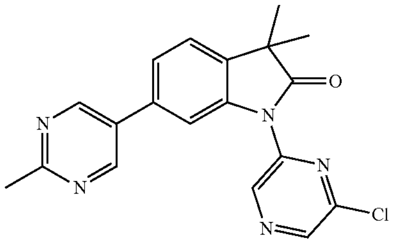 [SMILES: Cc1ncc(-c2ccc3c(c2)N(c2cncc(Cl)n2)C(=O)C3(C)C)cn1]

3,3-Dimethyl-6-(2-methylpyrimidin-5-yl)indolin-2-one (3 g, 11.8 mmol, Eq: 1, WO2014/202493 A1), 2-bromo-6-chloropyrazine (2.98 g, 15.4 mmol, Eq: 1.30), copper (I) iodide (226 mg, 1.18 mmol, Eq: 0.10), potassium carbonate (3.27 g, 23.7 mmol, Eq: 2) and trans-N,N-dimethylcyclohexane 1,2-diamine (347 mg, 385 μl, 2.37 mmol, Eq: 0.20) were combined with degassed 1,4-dioxane (30 ml) under inert atmosphere. The reaction mixture was heated to 110° C. and stirred for 20 h. The reaction mixture was poured into saturated sodium bicarbonate and extracted with ethyl acetate (2×). The organic layers were combined and washed with water and brine and finally dried over sodium sulfate then filtered and evaporated in vacuo. The residue was purified by chromatography on silica gel to afford the desired product as a white solid (2 g, 46%). MS (m/z)=366.2 [M+H]+.

b) 6-(3,3-Dimethyl-6-(2-methylpyrimidin-5-yl)-2-oxoindolin-1-yl)-N-methylpyrazine-2-carboxamide

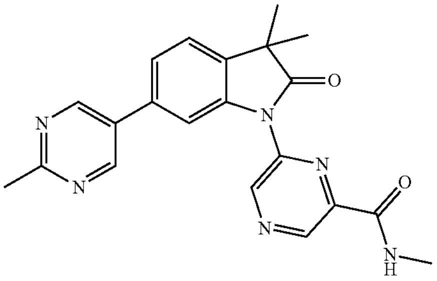

In a reactor autoclave, 1-(6-chloropyrazin-2-yl)-3,3-dimethyl-6-(2-methylpyrimidin-5-yl)indolin-2-one (1000 mg, 2.73 mmol, Eq: 1), 1,1-bis(diphenylphosphino)ferrocene-palladium(II)dichloride dichlormethane adduct (178 mg, 218 μmol, Eq: 0.0798), methylamine hydrochloride (277 mg, 4.1 mmol, Eq: 1.5), triethylamine (836 mg, 1.15 ml, 4.1 mmol, Eq: 3) were combined with tetrahydrofuran (20 ml) and stirred under 50 atmospheres of carbon monoxide at 110° C. for 18 h.

The crude reaction mixture was concentrated in vacuo and purified by chromatography on silica gel to afford the desired product as a white solid (900 mg, 84%).

MS (m/z)=389.3 [M+H]+.

Example 3

1-(6-(Azetidine-1-carbonyl)pyrazin-2-yl)-3,3-dimethyl-6-(2-methylpyrimidin-5-yl)indolin-2-one

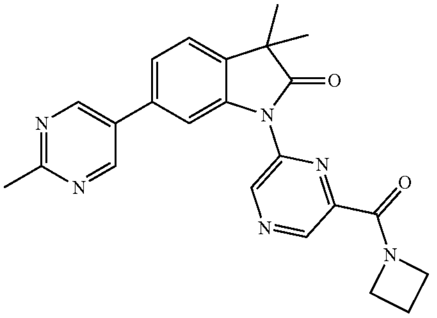 [SMILES: Cc1ncc(-c2ccc3c(c2)N(c2cncc(C(=O)N4CCC4)n2)C(=O)C3(C)C)cn1]

1-(6-Chloropyrazin-2-yl)-3,3-dimethyl-6-(2-methylpyrimidin-5-yl)indolin-2-one (140 mg, 383 Eq: 1, Example 2a), azetidine (26.8 mg, 31.6 μl, 459 μmol, Eq: 1.2), tributylamine (78 mg, 100 μl, 421 μmol, Eq: 1.1), tetraethylammonium chloride (12.7 mg, 76.5 μmol, Eq: 0.2) and molybden-hexacarbonyl (20.2 mg, 76.5 μmol, Eq: 0.2) were combined with diethylene glycol dimethyl ether (2.8 ml). The reaction mixture was heated to 150° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo.

The residue was purified by chromatography on silica gel, followed by preparative HPLC to afford the desired product as a white solid (28 mg, 17%). MS (m/z)=415.2 [M+H]+.

Example 4

6-(3,3-Dimethyl-6-(2-methylpyrimidin-5-yl)-2-oxoindolin-1-yl)-N-methyl-N-(2,2,2-trifluoroethyl)pyrazine-2-carboxamide

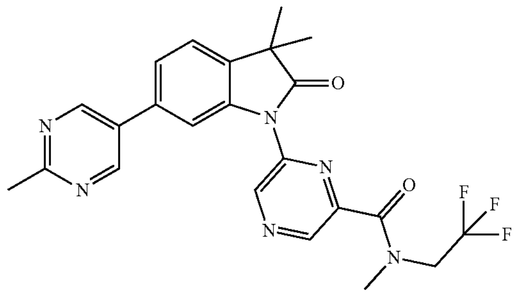 [SMILES: Cc1ncc(-c2ccc3c(c2)N(c2cncc(C(=O)N(C)CC(F)(F)F)n2)C(=O)C3(C)C)cn1]

1-(6-Chloropyrazin-2-yl)-3,3-dimethyl-6-(2-methylpyrimidin-5-yl)indolin-2-one (140 mg, 383 Eq: 1, Example 2a), methyl(2,2,2-trifluoroethyl)amine hydrochloride (68.7 mg, 459 μmol, Eq: 1.2), tributylamine (156 mg, 200 μl, 842 μmol, Eq: 2.2) tetraethylammonium chloride (12.7 mg, 76.5 μmol, Eq: 0.2), molybden-hexacarbonyl (20.2 mg, 76.5 μmol, Eq: 0.2) were combined with diethylene glycol dimethyl ether (2.8 ml). The reaction mixture was heated to 150° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo. The residue was purified by chromatography on silica gel, followed by preparative HPLC to afford the desired product as a white solid (25 mg, 13%). MS (m/z)=471.2 [M+H]+.

Example 5

6-(3,3-Dimethyl-6-(2-methylpyrimidin-5-yl)-2-oxoindolin-1-yl)-N-(2-methoxyethyl)-N-methylpyrazine-2-carboxamide

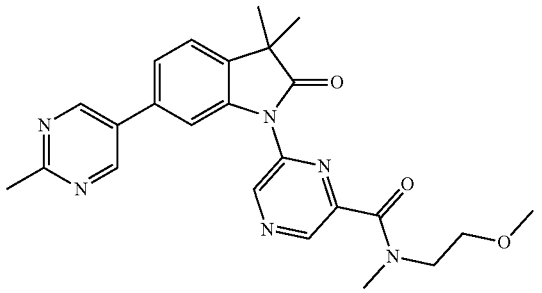

Example 5 was prepared from 1-(6-chloropyrazin-2-yl)-3,3-dimethyl-6-(2-methylpyrimidin-5-yl)indolin-2-one (Example 2a) and 2-methoxy-N-methylethanamine in analogy to example 3 to give the title compound (32%) as a colorless oil. MS (m/z)=447.2 [$(M+H)^+$].

Example 6

6-(3,3-Dimethyl-6-(2-methylpyrimidin-5-yl)-2-oxoindolin-1-yl)-N-(2-hydroxyethyl)pyrazine-2-carboxamide

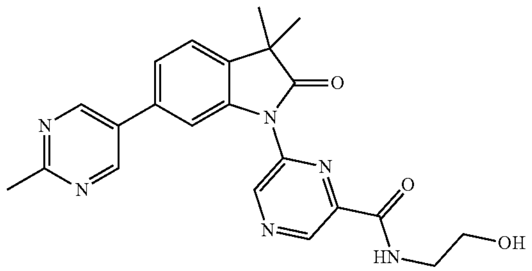 [SMILES: Cc1ncc(-c2ccc3c(c2)N(c2cncc(C(=O)NCCO)n2)C(=O)C3(C)C)cn1]

Example 6 was prepared from 1-(6-bromopyrazin-2-yl)-3,3-dimethyl-6-(2-methylpyrimidin-5-yl)indolin-2-one (Example 1a) and ethanolamine in analogy to example 3 to give the title compound (65%) as a white solid. MS (m/z)=419.3 [$(M+H)^+$].

Example 7

6-(3,3-Dimethyl-6-(2-methylpyrimidin-5-yl)-2-oxoindolin-1-yl)-N-(2-methoxyethyl)pyrazine-2-carboxamide

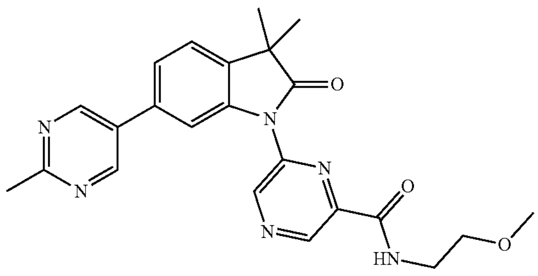

Example 7 was prepared from 1-(6-chloropyrazin-2-yl)-3,3-dimethyl-6-(2-methylpyrimidin-5-yl)indolin-2-one (Example 2a) and 2-methoxyethanamine in analogy to example 3 to give the title compound (36%) as a light yellow solid. MS (m/z)=433.2 [(M+H)+].

Example 8

6-(3,3-Dimethyl-6-(2-methylpyrimidin-5-yl)-2-oxoindolin-1-yl)-N-(2,2,2-trifluoroethyl)pyrazine-2-carboxamide

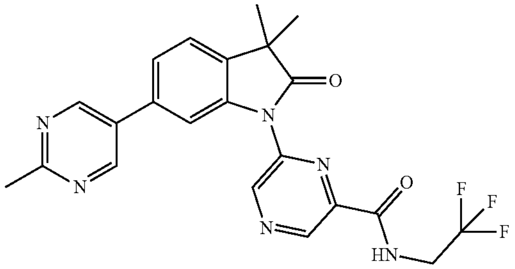 [SMILES: Cc1ncc(-c2ccc3c(c2)N(c2cncc(C(=O)NCC(F)(F)F)n2)C(=O)C3(C)C)cn1]

Example 8 was prepared from 1-(6-chloropyrazin-2-yl)-3,3-dimethyl-6-(2-methylpyrimidin-5-yl)indolin-2-one (Example 2a) and 2,2,2-trifluoroethanamine in analogy to example 3 to give the title compound (45%) as a light yellow solid. MS (m/z)=457.3 [(M+H)+].

Example 9

6-(3,3-Dimethyl-6-(2-methylpyrimidin-5-yl)-2-oxoindolin-1-yl)-N-isopropylpyrazine-2-carboxamide

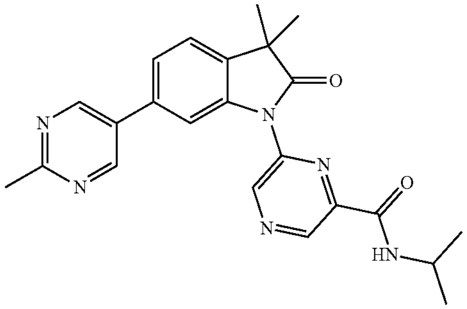 [SMILES: Cc1ncc(-c2ccc3c(c2)N(c2cncc(C(=O)NC(C)C)n2)C(=O)C3(C)C)cn1]

Example 9 was prepared from 1-(6-chloropyrazin-2-yl)-3,3-dimethyl-6-(2-methylpyrimidin-5-yl)indolin-2-one (Example 2a) and propan-2-amine in analogy to example 3 to give the title compound (50%) as a white solid. MS (m/z)=417.3 [(M+H)+].

Example 10

6-(3,3-Dimethyl-6-(2-methylpyrimidin-5-yl)-2-oxoindolin-1-yl)pyrazine-2-carboxamide

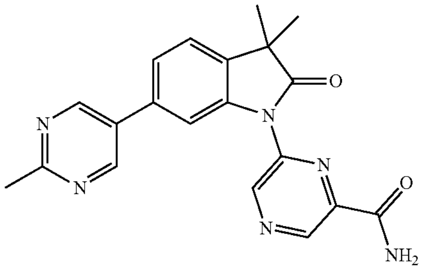 [SMILES: Cc1ncc(-c2ccc3c(c2)N(c2cncc(C(N)=O)n2)C(=O)C3(C)C)cn1]

1-(6-Chloropyrazin-2-yl)-3,3-dimethyl-6-(2-methylpyrimidin-5-yl)indolin-2-one (140 mg, 383 Eq: 1, Example 2a), ammonia 7M in MeOH (547 μl, 3.83 mmol, Eq: 10), tributylamine (78 mg, 100 μl, 421 μmol, Eq: 1.1), tetraethylammonium chloride (12.7 mg, 76.5 μmol, Eq: 0.2) and molybden-hexacarbonyl (20.2 mg, 76.5 μmol, Eq: 0.2) were combined with diethylene glycol dimethyl ether (2.8 ml). The reaction mixture was heated to 110° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo.

The residue was purified by chromatography on silica gel to afford the desired product as a white solid (20 mg, 14%), MS (m/z)=375.2 [M+H]+.

Example 11

5-[3,3-Dimethyl-6-(2-methylpyrimidin-5-yl)-2-oxoindol-1-yl]-dimethylpyrazine-2-carboxamide

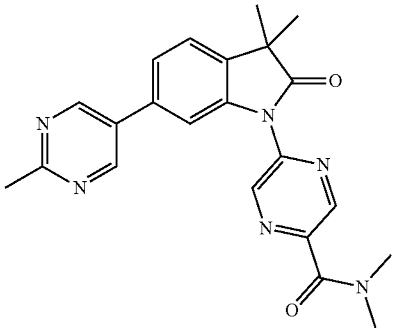

a) 1-(5-Bromopyrazin-2-yl)-3,3-dimethyl-6-(2-methylpyrimidin-5-yl)indolin-2-one

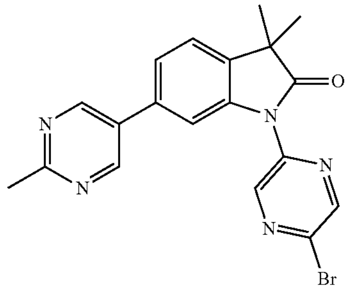 [SMILES: Cc1ncc(-c2ccc3c(c2)N(c2cnc(Br)cn2)C(=O)C3(C)C)cn1]

3,3-Dimethyl-6-(2-methylpyrimidin-5-yl)indolin-2-one (600 mg, 2.37 mmol, Eq: 1, WO2014/202493 A1), 2,5-dibromopyrazine (676 mg, 2.84 mmol, Eq: 1.2), copper (I) iodide (45.1 mg, 237 μmol, Eq: 0.1), trans-N,N-dimethyl-cyclohexane 1,2-diamine (67.4 mg, 74.7 μl, 474 μmol, Eq: 0.2) and potassium carbonate (655 mg, 4.74 mmol, Eq: 2) were dissolved in degassed 1,4-dioxane (8 ml). The reaction mixture was heated to 100° C. for 16 h under inert atmosphere. The reaction mixture was poured into saturated sodium carbonate and extracted with ethyl acetate (2×). The organic layers were combined and washed with water and brine and finally dried over sodium sulfate then filtered and evaporated in vacuo.

The residue was purified by chromatography on silica gel to afford the desired product as a white solid (328 mg, 33%), MS (m/z)=412.2 [M+H]+.

b) 5-[3,3-Dimethyl-6-(2-methylpyrimidin-5-yl)-2-oxoindol-1-yl]-dimethylpyrazine-2-carboxamide

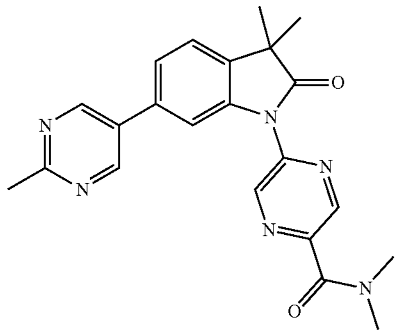

1-(5-Bromopyrazin-2-yl)-3,3-dimethyl-6-(2-methylpyrimidin-5-yl)indolin-2-one (328 mg, 799 Eq: 1), dimethylamine hydrochloride (97.8 mg, 1.2 mmol, Eq: 1.5), tributylamine (445 mg, 570 μl, 2.4 mmol, Eq: 3.00), tetraethylammonium chloride (24.8 mg, 150 μmol, Eq: 0.187) and molybden-hexacarbonyl (58.8 mg, 223 μmol, Eq: 0.278) were combined with diethylene glycol dimethyl ether (6.56 ml). The reaction mixture was heated to 150° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo.

The residue was purified by chromatography on silica gel to afford the desired product as a white solid (105 mg, 32%), MS (m/z)=403.2 [M+H]+.

Example 12

N-(tert-Butyl)-5-(3,3-dimethyl-6-(2-methylpyrimidin-5-yl)-2-oxoindolin-1-yl)-N-methylpyrazine-2-carboxamide

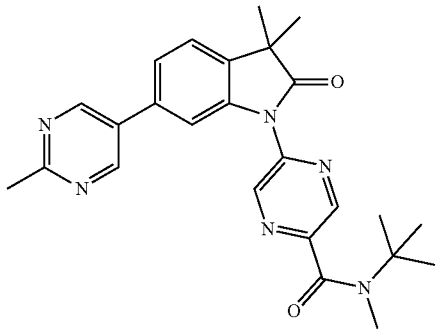 [SMILES: Cc1ncc(-c2ccc3c(c2)N(c2cnc(C(=O)N(C)C(C)(C)C)cn2)C(=O)C3(C)C)cn1]

3,3-Dimethyl-6-(2-methylpyrimidin-5-yl)indolin-2-one (200 mg, 790 μmol, Eq: 1, WO2014/202493 A1), 5-bromo-N-(tert-butyl)-N-methylpyrazine-2-carboxamide (322 mg, 1.18 mmol, Eq: 1.50), potassium carbonate (218 mg, 1.58 mmol, Eq: 2.00), copper (I) iodide (15 mg, 79 μmol, Eq: 0.10) and N1,N2-dimethylethane-1,2-diamine (14.1 mg, 17.2 μl, 158 μmol, Eq: 0.20) were combined with degassed acetonitrile (6 ml) under nitrogen atmosphere. The reaction mixture was heated to 100° C. and stirred for 24 h. The crude reaction mixture was cooled to room temperature, then diluted with ethyl acetate and washed with saturated sodium carbonate and water. The organic phases were combined and washed with brine, dried over sodium sulfate then filtered and evaporated in vacuo.

The residue was purified by chromatography on silica gel to afford the desired product as a white solid (320 mg, 91%). MS (m/z)=445.3 [M+H]+

Example 13

1-(5-(Azetidine-1-carbonyl)pyrazin-2-yl)-3,3-dimethyl-6-(2-methylpyrimidin-5-yl)indolin-2-one

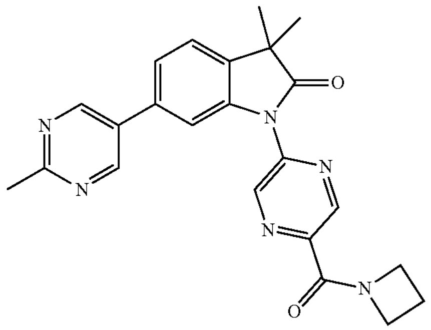 [SMILES: Cc1ncc(-c2ccc3c(c2)N(c2cnc(C(=O)N4CCC4)cn2)C(=O)C3(C)C)cn1]

1-(5-Bromopyrazin-2-yl)-3,3-dimethyl-6-(2-methylpyrimidin-5-yl)indolin-2-one (140 mg, 341 Eq: 1, Example 11a), azetidine (28.2 μl, 409 μmol, Eq: 1.2), tributylamine (69.6 mg, 89.2 μl, 375 μmol, Eq: 1.1), tetraethylammonium chloride (11.3 mg, 68.2 μmol, Eq: 0.2) and molybdenhexacarbonyl (18 mg, 68.2 μmol, Eq: 0.2) were combined with diethylene glycol dimethyl ether (2.8 ml). The reaction mixture was heated to 150° C. and stirred for 20 h. The crude reaction mixture was concentrated in vacuo and then diluted with ethyl acetate and washed with 1N hydrochloric acid and water. The combined organic phases were washed with brine, dried over sodium sulfate then filtered and evaporated in vacuo.

The residue was purified by chromatography on silica gel, followed by prep HPLC to afford the desired product as a white solid (27 mg, 19%), MS (m/z)=415.2 [M+H]+.

Example 14

5-(3,3-Dimethyl-6-(2-methylpyrimidin-5-yl)-2-oxoindolin-1-yl)-N-(2-methoxyethyl)-N-methylpyrazine-2-carboxamide

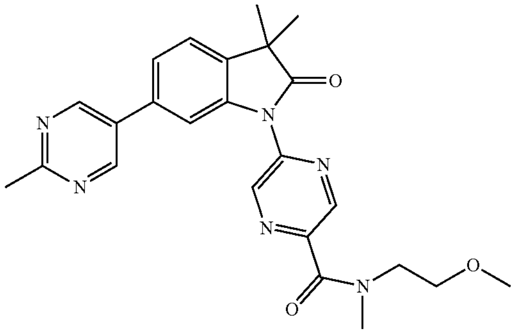

Example 14 was prepared from 1-(5-bromopyrazin-2-yl)-3,3-dimethyl-6-(2-methylpyrimidin-5-yl)indolin-2-one (example 11a) and 2-methoxy-N-methylethanamine in analogy to example 13 to give the title compound (26%) as a light yellow solid. MS (m/z)=447.3 [(M+H)+].

Example 15

5-(3,3-Dimethyl-6-(2-methylpyrimidin-5-yl)-2-oxoindolin-1-yl)pyrazine-2-carboxamide

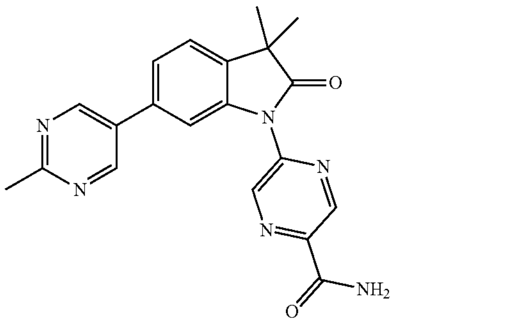 [SMILES: Cc1ncc(-c2ccc3c(c2)N(c2cnc(C(N)=O)cn2)C(=O)C3(C)C)cn1]

Example 15 was prepared from 1-(5-bromopyrazin-2-yl)-3,3-dimethyl-6-(2-methylpyrimidin-5-yl)indolin-2-one (example 11a) in analogy to example 10 to give the title compound (29%) as a white solid. MS (m/z)=375.2 [(M+H)+].

Example 16

2-(3,3-Dimethyl-6-(2-methylpyrimidin-5-yl)-2-oxoindolin-1-yl)-N-methylpyrimidine-4-carboxamide

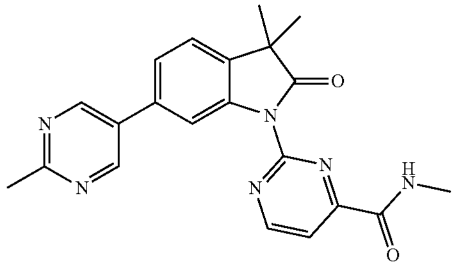

a) 2-Chloro-N-methylpyrimidine-4-carboxamide

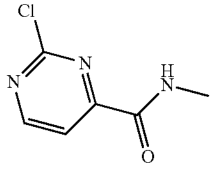

2-Chloropyrimidine-4-carboxylic acid (100 mg, 631 μmol, Eq: 1), thionyl chloride (82.5 mg, 50.6 μl, 694 μmol, Eq: 1.1) and dimethylformamide (4.61 mg, 4.88 μl, 63.1 μmol, Eq: 0.1) were combined with toluene (2.1 ml). The reaction mixture was heated to 120° C. and stirred for 2 h. The crude reaction mixture was concentrated in vacuo. The reaction mixture was diluted with dichloromethane (4.2 ml). N,N-Diisopropylethylamine (245 mg, 330 μl, 1.89 mmol, Eq: 3) and methanamine hydrochloride (46.8 mg, 694 μmol, Eq: 1.1) were added at 0° C. The reaction mixture was stirred at room temperature for 1.5 h. The reaction mixture was poured into water (25 ml) and extracted with dichloromethane (2×20 mL). The organic layers were dried over sodium sulfate and concentrated in vacuo.

The residue was purified by chromatography on silica gel to afford the desired product as a white solid (78 mg, 72%). MS (m/z)=172.2 [M+H]+.

b) 2-(3,3-Dimethyl-6-(2-methylpyrimidin-5-yl)-2-oxoindolin-1-yl)-N-methylpyrimidine-4-carboxamide

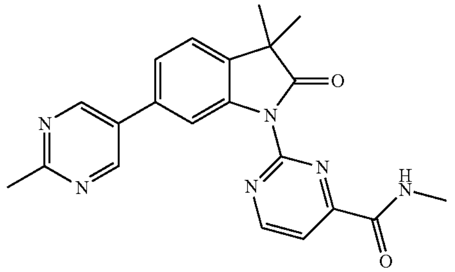

In a pressure tube, argon was bubbled through a suspension of 3,3-dimethyl-6-(2-methylpyrimidin-5-yl)indolin-2-one (100 mg, 395 μmol, Eq: 1, WO2014/202493 A1), 2-chloro-N-methylpyrimidine-4-carboxamide (75 mg, 437 μmol, Eq: 1.11) and cesium carbonate (193 mg, 592 μmol, Eq: 1.5) in 1,4-dioxane (3.95 ml) for 5 minutes. xantphos (22.8 mg, 39.5 μmol, Eq: 0.1) and tris(dibenzylideneacetone)dipalladium (0) (36.2 mg, 39.5 μmol, Eq: 0.1) were added and the tube was sealed and the reaction mixture was heated to 110° C. overnight under argon atmosphere. Xantphos (22.8 mg, 39.5 μmol, Eq: 0.1) and tris(dibenzylideneacetone)dipalladium (0) (36.2 mg, 39.5 μmol, Eq: 0.1) were added again under an argon atmosphere and the reaction mixture was heated to 110° C. for 24 h.

The residue was evaporated in vacuo and purified by chromatography on silica gel to afford the desired product as a light yellow solid (110 mg, 71%), MS (m/z)=389.2 [M+H]+.

Example 17

2-(3,3-Dimethyl-6-(2-methylpyrimidin-5-yl)-2-oxoindolin-1-yl)-N,N-dimethylpyrimidine-4-carboxamide

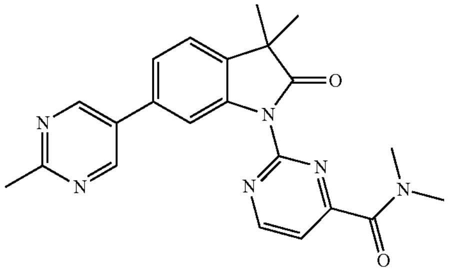

a) 2-Chloro-N,N-dimethylpyrimidine-4-carboxamide

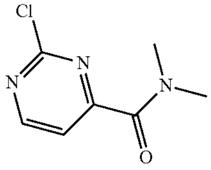

Example 17a was prepared from 2-chloropyrimidine-4-carboxylic acid with dimethylamine hydrochloride in analogy to example 16a to give the title compound (73%) as a brown solid.

MS (m/z)=186.1 [(M+H)$^+$].

b) 2-(3,3-Dimethyl-6-(2-methylpyrimidin-5-yl)-2-oxoindolin-1-yl)-N,N-dimethylpyrimidine-4-carboxamide

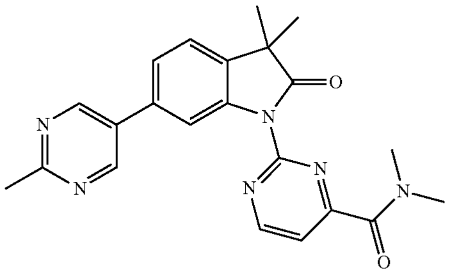

Example 17b was prepared from 3,3-dimethyl-6-(2-methylpyrimidin-5-yl)indolin-2-one (WO2014/202493 A1) with 2-chloro-N,N-dimethylpyrimidine-4-carboxamide in analogy to example 16b to give the title compound (68%) as a yellow solid. MS (m/z)=403.3 [(M+H)$^+$].

Example 18

2-(3,3-Dimethyl-6-(2-methylpyrimidin-5-yl)-2-oxoindolin-1-yl)-N,5-dimethylpyrimidine-4-carboxamide

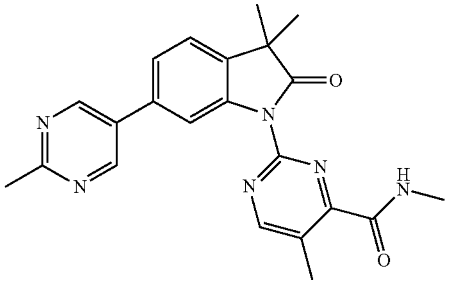

a) 2-Chloro-N,5-dimethylpyrimidine-4-carboxamide

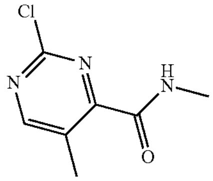

2-Chloro-5-methylpyrimidine-4-carboxylic acid (40 mg, 232 μmol, Eq: 1), oxalyl chloride (88.3 mg, 60.9 μl, 695 μmol, Eq: 3) and dimethylformamide (1.69 mg, 1.79 μl, 23.2 μmol, Eq: 0.1) were combined with dichloromethane (2.32 ml). The reaction mixture was stirred at room temperature for 4 h. The crude reaction mixture was concentrated in vacuo. The reaction mixture was diluted with dichloromethane (2.32 ml) and N,N-diisopropylethylamine (89.9 mg, 121 μl, 695 μmol, Eq: 3) and methanamine hydrochloride (17.2 mg, 255 μmol, Eq: 1.1) were added at 0° C. The reaction mixture was stirred at room temperature for 1.5 h. The reaction mixture was poured into water (25 ml) and extracted with dichloromethane (2×20 mL). The organic layers were dried over sodium sulfate, filtered and concentrated in vacuo.

The residue was purified by chromatography on silica gel to afford the desired product as a white solid (46 mg, 100%). MS (m/z)=186.1 [M+H]+.

b) 2-(3,3-Dimethyl-6-(2-methylpyrimidin-5-yl)-2-oxoindolin-1-yl)-N,5-dimethylpyrimidine-4-carboxamide

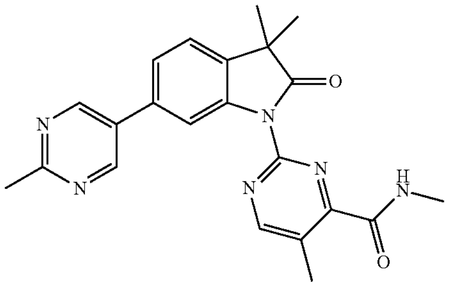

Example 18b was prepared from 3,3-dimethyl-6-(2-methylpyrimidin-5-yl)indolin-2-one (WO2014/202493 A1) with 2-chloro-N,5-dimethylpyrimidine-4-carboxamide in analogy to example 16b to give the title compound (58%) as a light brown solid.

MS (m/z)=403.3 [(M+H)$^+$].

Example 19

4-(3,3-Dimethyl-6-(2-methylpyrimidin-5-yl)-2-oxoindolin-1-yl)-N,N-dimethylpyrimidine-2-carboxamide

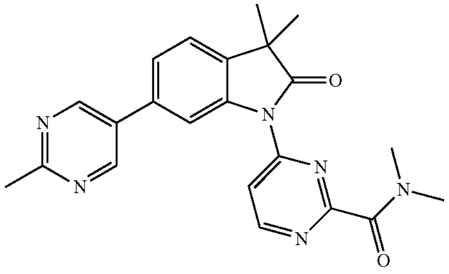

a) 4-Chloro-N,N-dimethylpyrimidine-2-carboxamide

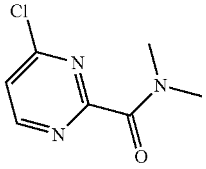

4-Chloropyrimidine-2-carboxylic acid (600 mg, 3.78 mmol, Eq: 1), 2-(1H-benzo[d][1,2,3]triazol-1-yl)-1,1,3,3-tetramethylisouronium tetrafluoroborate (1.46 g, 4.54 mmol, Eq: 1.20) and N,N-diisopropylethylamine (2.5 g, 3.37 ml, 18.9 mmol, Eq: 5.00) were combined with dry dimethylformamide (10 ml). The reaction mixture was stirred at room temperature for 40 min, then dimethylamine hydrochloride (346 mg, 4.16 mmol, Eq: 1.10) was added. The reaction mixture was stirred at 22° C. for 16 h. The crude reaction mixture was concentrated in vacuo. The residue was diluted with saturated sodium bicarbonate and extracted with dichloromethane (×2). The combined organic layers were washed with brine, dried over sodium sulfate then filtered and evaporated in vacuo.

The residue was purified by chromatography on silica gel to afford the desired product as an orange oil (8%). MS (m/z)=186.1 [M+H]+.

b) 4-(3,3-Dimethyl-6-(2-methylpyrimidin-5-yl)-2-oxoindolin-1-yl)-N,N-dimethylpyrimidine-2-carboxamide

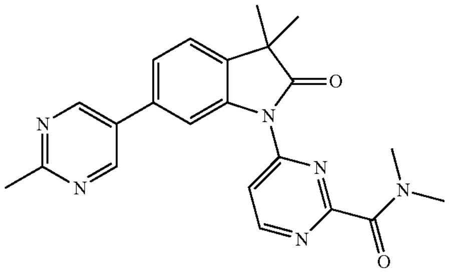

3,3-Dimethyl-6-(2-methylpyrimidin-5-yl)indolin-2-one (70 mg, 276 μmol, Eq: 1, WO2014/202493 A1) and sodium hydride (12.2 mg, 304 μmol, Eq: 1.10) were combined with dimethylacetamide (2 ml). 4-Chloro-N,N-dimethylpyrimidine-2-carboxamide (56.4 mg, 304 μmol, Eq: 1.10) was added after 10 min. The reaction mixture was heated to 110° C. and stirred for 24 h under nitrogen atmosphere. The crude reaction mixture was concentrated in vacuo. The residue was diluted with saturated sodium bicarbonate and extracted with ethyl acetate (2×). The combined organic phases were washed with water and brine, dried over sodium sulfate then filtered and evaporated in vacuo.

The residue was purified by chromatography on silica gel to afford the desired product as a yellow solid (15 mg, 12%). MS (m/z)=403.2 [M+H]+.

Example 20

4-(3,3-Dimethyl-6-(2-methylpyrimidin-5-yl)-2-oxoindolin-1-yl)-N-methylpyrimidine-2-carboxamide

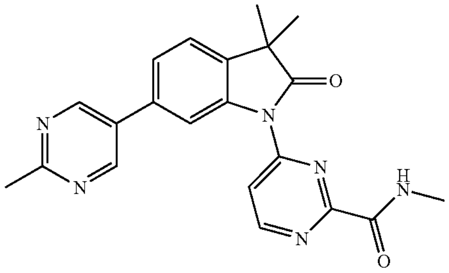

a) 4-(3,3-Dimethyl-6-(2-methylpyrimidin-5-yl)-2-oxoindolin-1-yl)pyrimidine-2-carboxylic acid

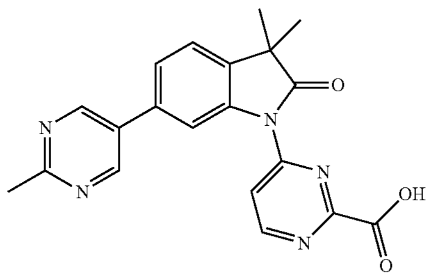 [SMILES: Cc1ncc(-c2ccc3c(c2)N(c2ccnc(C(=O)O)n2)C(=O)C3(C)C)cn1]

3,3-Dimethyl-6-(2-methylpyrimidin-5-yl)indolin-2-one (150 mg, 592 μmol, Eq: 1, WO2014/202493 A1) was combined with dimethylformamide (2 ml). Sodium hydride (59.2 mg, 1.48 mmol, Eq: 2.50) was added. The reaction mixture was stirred at room temperature for 30 min then 4-chloropyrimidine-2-carboxylic acid (98.6 mg, 622 μmol, Eq: 1.05) was added and stirring was continued at room temperature overnight then at 80° C. for 24 h. The crude reaction mixture was concentrated in vacuo. The residue was poured into saturated sodium bicarbonate and washed with ethyl acetate (2×). The aqueous layer was acidified with hydrochloric acid 2N and then back-extracted with ethyl acetate (3×). The organic layers were combined and dried over sodium sulfate then filtered and evaporated in vacuo to afford the desired product as a yellow solid (135 mg, 48%). MS (m/z)=376.2 [M+H]+.

b) 4-(3,3-Dimethyl-6-(2-methylpyrimidin-5-yl)-2-oxoindolin-1-yl)-N-methylpyrimidine-2-carboxamide

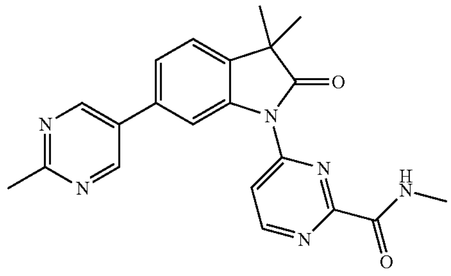

4-(3,3-Dimethyl-6-(2-methylpyrimidin-5-yl)-2-oxoindolin-1-yl)pyrimidine-2-carboxylic acid (70 mg, 186 μmol, Eq: 1), O-(benzotriazol-1-yl)-N,N,N',N'-tetramethyluronium tetrafluoroborate (92.6 mg, 280 μmol, Eq: 1.50) and N,N-diisopropylethylamine (72.3 mg, 97.7 μl, 559 μmol, Eq: 3.00) were combined with dimethylformamide (3 ml). The reaction mixture was stirred for 30 min then methanamine 2M in tetrahydrofuran (112 μl, 224 μmol, Eq: 1.20) was added and stirring was continued at room temperature for 16 h. Then 1 equivalent of each reactant were added again and stirring was continued at room temperature for another 24 h. The crude reaction mixture was concentrated in vacuo. The crude was then diluted with saturated sodium bicarbonate and extracted with ethyl acetate (2×). The combined organic phases were washed with brine, dried over sodium sulfate then filtered and evaporated in vacuo. The residue was purified by chromatography on silica gel to afford the desired product as a white foam (20 mg, 24%). MS (m/z)=389.3 [M+H]+.

Example 21

6-(3,3-Dimethyl-6-(2-methylpyrimidin-5-yl)-2-oxoindolin-1-yl)-N,N-dimethylpyridazine-3-carboxamide

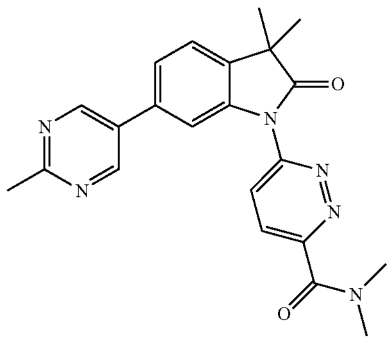

a) 6-(3,3-Dimethyl-6-(2-methylpyrimidin-5-yl)-2-oxoindolin-1-yl)pyridazine-3-carboxylic acid

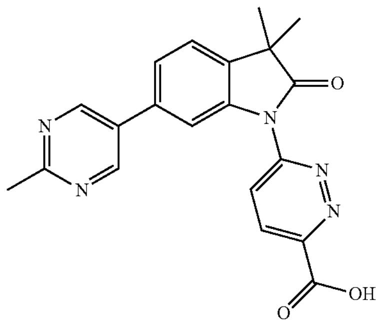 [SMILES: Cc1ncc(-c2ccc3c(c2)N(c2ccc(C(=O)O)nn2)C(=O)C3(C)C)cn1]

3,3-Dimethyl-6-(2-methylpyrimidin-5-yl)indolin-2-one (500 mg, 1.97 mmol, Eq: 1, WO2014/202493 A1) was combined with dimethylacetamide (6 ml). Potassium carbonate (409 mg, 2.96 mmol, Eq: 1.50) then methyl 6-chloropyridazine-3-carboxylate (443 mg, 2.57 mmol, Eq: 1.30) were added. The reaction mixture was heated to 110° C. and stirred for 3 days. The reaction mixture was concentrated in vacuo. The residue was taken into saturated sodium bicarbonate and washed with ethyl acetate (2×). The aqueous layer was acidified with hydrochloric acid 2N and then back-extracted with ethyl acetate (3×). The organic layers were combined, dried over sodium sulfate then filtered and evaporated in vacuo to afford the desired product as a brown oil (29%). MS (m/z)=376.2 [M+H]+.

b) 6-(3,3-Dimethyl-6-(2-methylpyrimidin-5-yl)-2-oxoindolin-1-yl)-N,N-dimethylpyridazine-3-carboxamide

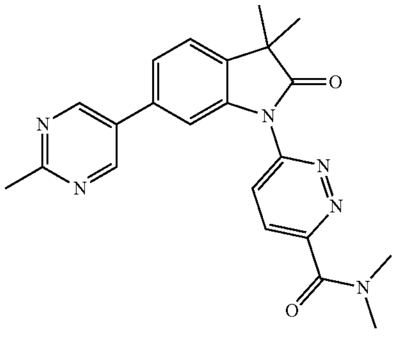

6-(3,3-Dimethyl-6-(2-methylpyrimidin-5-yl)-2-oxoindolin-1-yl)pyridazine-3-carboxylic acid (215 mg, 573 μmol, Eq: 1), 1-[bis(dimethylamino)methylene]-1H-1,2,3-triazolo [4,5-b]pyridinium 3-oxid hexafluorophosphate (444 mg, 1.15 mmol, Eq: 2.00) and N,N-diisopropylethylamine (453 mg, 612 μl, 3.44 mmol, Eq: 6.00) were combined with dimethylformamide (4 ml). The reaction mixture was stirred at room temperature for 30 min then dimethylamine hydrochloride (71.5 mg, 859 μmol, Eq: 1.50) was added and stirring was continued at room temperature for 16 h. The reaction mixture was concentrated in vacuo. The residue was then diluted with saturated sodium bicarbonate and extracted with ethyl acetate (2×). The combined organic layers were washed with brine, dried over sodium sulfate then filtered and evaporated in vacuo.

The residue was purified by chromatography on silica gel, followed by prep HPLC to afford the desired product as a white solid (30 mg, 13%). MS (m/z)=403.3 [M+H]+.

Example 22

6-(3,3-Dimethyl-6-(2-methylpyrimidin-5-yl)-2-oxoindolin-1-yl)-N-methylpicolinamide

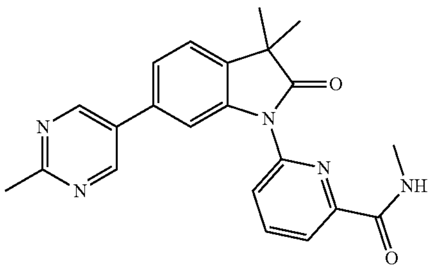 [SMILES: CNC(=O)c1cccc(N2C(=O)C(C)(C)c3ccc(-c4cnc(C)nc4)cc32)n1]

In a pressure tube, argon was bubbled through a suspension of 3,3-dimethyl-6-(2-methylpyrimidin-5-yl)indolin-2-one (50 mg, 197 μmol, Eq: 1, WO2014/202493 A1), 6-chloro-N-methylpicolinamide (40.4 mg, 237 μmol, Eq: 1.2) and cesium carbonate (83.6 mg, 257 μmol, Eq: 1.3) in dioxane (9870) for 5 minutes. Xantphos (22.8 mg, 39.5 μmol, Eq: 0.2) and tris(dibenzylideneacetone)dipalladium (0) (36.2 mg, 39.5 μmol, Eq: 0.2) were added and the reaction mixture was heated to 120° C. for 1 day under argon.

The residue was evaporated in vacuo and purified by chromatography on silica gel, followed by prep HPLC to afford the desired product as a light yellow solid (45 mg, 58%).

MS (m/z)=388.2 [M+H]+.

Example 23

6-(3,3-Dimethyl-6-(2-methylpyrimidin-5-yl)-2-oxoindolin-1-yl)-N,N-dimethylpicolinamide

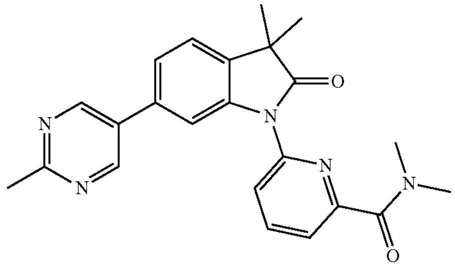

a) 6-Bromo-N,N-dimethylpicolinamide

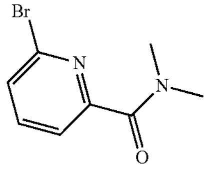

Example 23a was prepared from 6-bromopicolinic acid with dimethyl amine hydrochloride in analogy to example 16a to give the title compound (64%) as a yellow oil.

MS (m/z)=229/231 [(M+H)$^+$].

b) 6-(3,3-Dimethyl-6-(2-methylpyrimidin-5-yl)-2-oxoindolin-1-yl)-N,N-dimethylpicolinamide

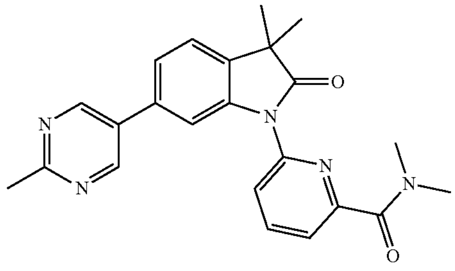

In a pressure tube, argon was bubbled through a suspension of 3,3-dimethyl-6-(2-methylpyrimidin-5-yl)indolin-2-one (80 mg, 316 μmol, Eq: 1, WO2014/202493 A1), 6-bromo-N,N-dimethylpicolinamide (109 mg, 474 μmol, Eq: 1.5) and potassium carbonate (87.3 mg, 632 μmol, Eq: 2) in acetonitrile (1.58 ml) for 5 minutes. Copper (I) iodide (12 mg, 63.2 μmol, Eq: 0.2) and N,N'-dimethylethylenediamine (7.59 mg, 8.45 μl, 126 μmol, Eq: 0.4) were added, the tube was sealed and the reaction mixture was heated to 120°

C. overnight under argon. The residue was evaporated in vacuo and purified by chromatography on silica gel to afford the desired product as a light yellow solid (125 mg, 95%), MS (m/z)=402.3 [M+H]+.

Example 24

N-Cyclopropyl-6-(3,3-dimethyl-6-(2-methylpyrimidin-5-yl)-2-oxoindolin-1-yl)picolinamide

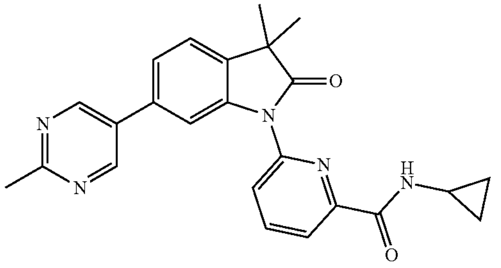 [SMILES: Cc1ncc(-c2ccc3c(c2)N(c2cccc(C(=O)NC4CC4)n2)C(=O)C3(C)C)cn1]

a) 6-Bromo-N-cyclopropylpicolinamide

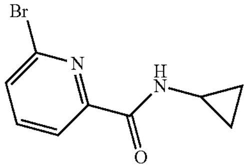 [SMILES: O=C(NC1CC1)c1cccc(Br)n1]

Example 24a was prepared from 6-bromopicolinic acid with cyclopropanamine in analogy to example 16a to give the title compound (70%) as a yellow viscous oil.

MS (m/z)=241/243 [(M+H)$^+$].

b) N-Cyclopropyl-6-(3,3-dimethyl-6-(2-methylpyrimidin-5-yl)-2-oxoindolin-1-yl)picolinamide

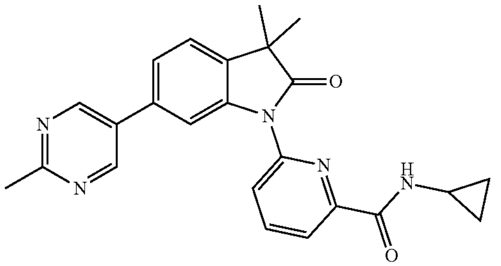 [SMILES: Cc1ncc(-c2ccc3c(c2)N(c2cccc(C(=O)NC4CC4)n2)C(=O)C3(C)C)cn1]

Example 24b was prepared from 3,3-dimethyl-6-(2-methylpyrimidin-5-yl)indolin-2-one (from WO2014/202493 A1) with 6-bromo-N-cyclopropylpicolinamide in analogy to example 23b to give the title compound (98%) as a light yellow foam. MS (m/z)=414.3 [(M+H)$^+$].

Example 25

N-(Cyclopropylmethyl)-6-(3,3-dimethyl-6-(2-methylpyrimidin-5-yl)-2-oxoindolin-1-yl)picolinamide

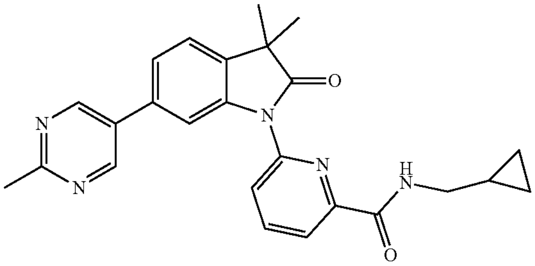 [SMILES: Cc1ncc(-c2ccc3c(c2)N(c2cccc(C(=O)NCC4CC4)n2)C(=O)C3(C)C)cn1]

a) 6-Bromo-N-(cyclopropylmethyl)picolinamide

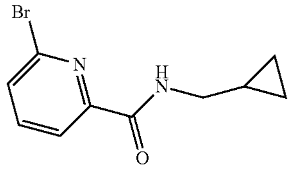 [SMILES: O=C(NCC1CC1)c1cccc(Br)n1]

Example 24a was prepared from 6-bromopicolinic acid with cyclopropylmethanamine hydrochloride in analogy to example 16a to give the title compound (72%) as a light yellow solid. MS (m/z)=255/257 [(M+H)$^+$].

b) N-(Cyclopropylmethyl)-6-(3,3-dimethyl-6-(2-methylpyrimidin-5-yl)-2-oxoindolin-1-yl)picolinamide

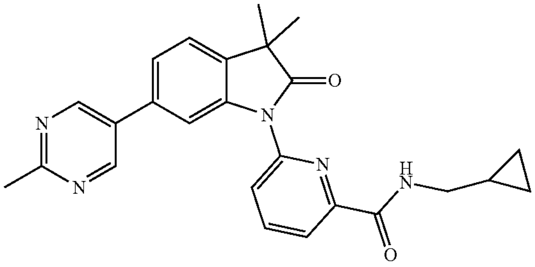 [SMILES: Cc1ncc(-c2ccc3c(c2)N(c2cccc(C(=O)NCC4CC4)n2)C(=O)C3(C)C)cn1]

Example 25b was prepared from 3,3-dimethyl-6-(2-methylpyrimidin-5-yl)indolin-2-one (from WO2014/202493 A1) with 6-bromo-N-(cyclopropylmethyl)picolinamide in analogy to example 23b to give the title compound (99%) as a light yellow foam. MS (m/z)=428.3 [(M+H)$^+$].

Example 26

6-(3,3-Dimethyl-6-(2-methylpyrimidin-5-yl)-2-oxoindolin-1-yl)picolinamide

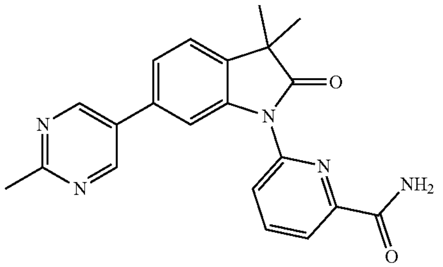 [SMILES: Cc1ncc(-c2ccc3c(c2)N(c2cccc(C(N)=O)n2)C(=O)C3(C)C)cn1]

Example 26 was prepared from 3,3-dimethyl-6-(2-methylpyrimidin-5-yl)indolin-2-one (from WO2014/202493 A1) with 6-bromopicolinamide in analogy to example 23b to give the title compound (49%) as a white solid. MS (m/z)=374.2 [(M+H)$^+$].

Example 27

6-(3,3-Dimethyl-6-(2-methylpyrimidin-5-yl)-2-oxoindolin-1-yl)-N,3-dimethylpicolinamide

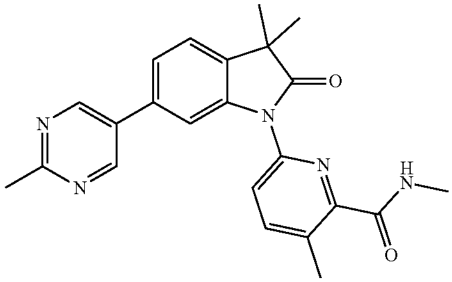

a) 6-Chloro-N,3-dimethylpicolinamide

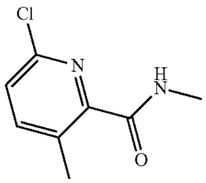

Example 27a was prepared from 6-chloro-3-methylpicolinic acid with methanamine hydrochloride in analogy to example 16a to give the title compound (70%) as a white solid. MS (m/z)=185.0 [(M+H)$^+$].

b) 6-(3,3-Dimethyl-6-(2-methylpyrimidin-5-yl)-2-oxoindolin-1-yl)-N,3-dimethylpicolinamide

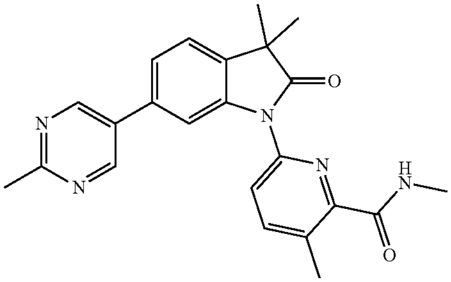

Example 27b was prepared from 3,3-dimethyl-6-(2-methylpyrimidin-5-yl)indolin-2-one (from WO2014/202493 A1) with 6-chloro-N,3-dimethylpicolinamide in analogy to example 22 to give the title compound (79%) as an orange solid. MS (m/z)=402.3 [(M+H)$^+$].

Example 28

6-(3,3-Dimethyl-6-(2-methylpyrimidin-5-yl)-2-oxoindolin-1-yl)-N,N,3-trimethylpicolinamide

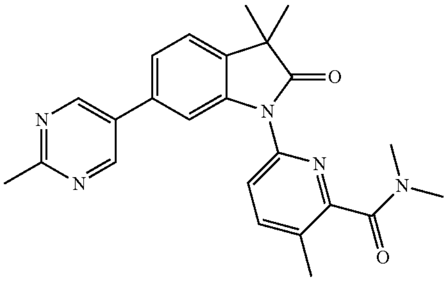

a) 6-Chloro-N,N,3-trimethylpicolinamide

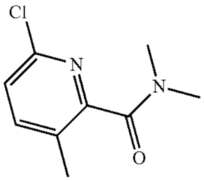

Example 28a was prepared from 6-chloro-3-methylpicolinic acid with dimethylamine hydrochloride in analogy to example 16a to give the title compound (77%) as a light yellow solid. MS (m/z)=199.1 [(M+H)$^+$].

b) 6-(3,3-Dimethyl-6-(2-methylpyrimidin-5-yl)-2-oxoindolin-1-yl)-N,N,3-trimethylpicolinamide

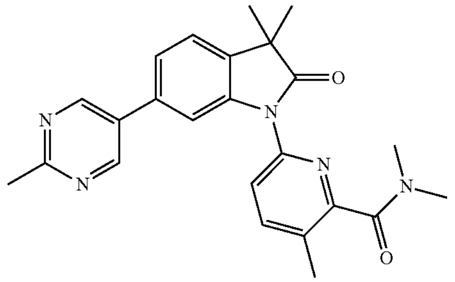

Example 28b was prepared from 3,3-dimethyl-6-(2-methylpyrimidin-5-yl)indolin-2-one (from WO2014/202493 A1) with 6-chloro-N,N,3-trimethylpicolinamide in analogy to example 22 to give the title compound (91%) as a light yellow solid. MS (m/z)=416.2 [(M+H)$^+$].

Example 29

6-(3,3-Dimethyl-6-(2-methylpyrimidin-5-yl)-2-oxoindolin-1-yl)-N,N-dimethylnicotinamide

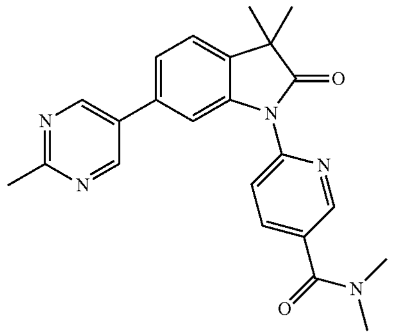

3,3-Dimethyl-6-(2-methylpyrimidin-5-yl)indolin-2-one (100 mg, 395 μmol, Eq: 1, WO2014/202493 A1) was combined with dimethylacetamide (2 ml). Potassium carbonate (109 mg, 790 μmol, Eq: 2.00) and 6-chloro-N,N-dimethylnicotinamide (87.5 mg, 474 μmol, Eq: 1.20) were added. The reaction mixture was heated to 110° C. and stirred for more than 4 days. The reaction mixture was poured into saturated sodium bicarbonate and extracted with ethyl acetate (2×). The organic layers were combined and washed with water and brine. The organic phase was dried over sodium sulfate then filtered and evaporated in vacuo.

The residue was purified by chromatography on silica gel to afford the desired product as a white foam (70 mg, 44%). MS (m/z)=402.3 [M+H]+.

Example 30

5-(3,3-Dimethyl-6-(2-methylpyrimidin-5-yl)-2-oxoindolin-1-yl)-N,N-dimethylnicotinamide

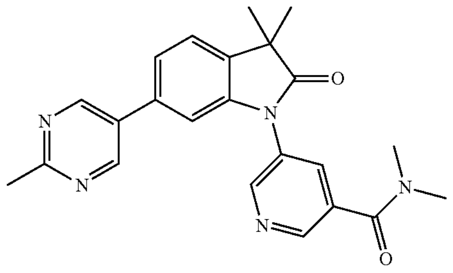

Example 30 was prepared from 3,3-dimethyl-6-(2-methylpyrimidin-5-yl)indolin-2-one (from WO2014/202493 A1) with 5-bromo-N,N-dimethylnicotinamide ([292170-96-8]) in analogy to example 1a to give the title compound (56%) as a white solid. MS (m/z)=402.2 [(M+H)$^+$].

Example 31

1-(5-(Azetidine-1-carbonyl)pyridin-3-yl)-3,3-dimethyl-6-(2-methylpyrimidin-5-yl)indolin-2-one

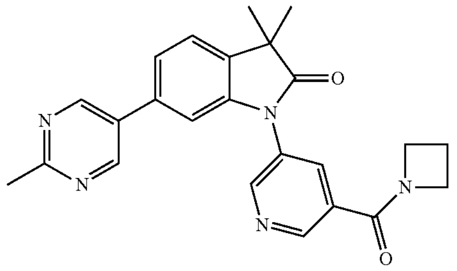 [SMILES: Cc1ncc(-c2ccc3c(c2)N(c2cncc(C(=O)N4CCC4)c2)C(=O)C3(C)C)cn1]

a) Azetidin-1-yl(5-bromopyridin-3-yl)methanone

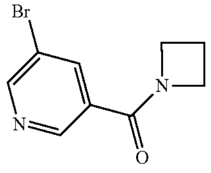 [SMILES: O=C(c1cncc(Br)c1)N1CCC1]

Example 31a was prepared from 5-bromonicotinic acid with azetidine in analogy to example 19a to give the title compound (87%) as a yellow solid. MS (m/z)=242.9 [(M+H)$^+$].

b) 1-(5-(Azetidine-1-carbonyl)pyridin-3-yl)-3,3-dimethyl-6-(2-methylpyrimidin-5-yl)indolin-2-one

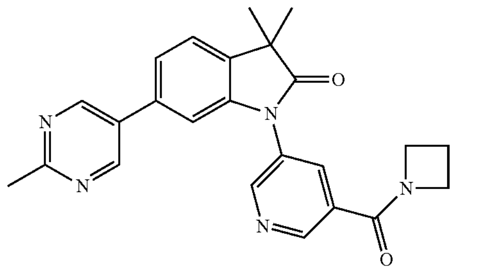 [SMILES: Cc1ncc(-c2ccc3c(c2)N(c2cncc(C(=O)N4CCC4)c2)C(=O)C3(C)C)cn1]

Example 31b was prepared from 3,3-dimethyl-6-(2-methylpyrimidin-5-yl)indolin-2-one (from WO2014/202493 A1) with azetidin-1-yl(5-bromopyridin-3-yl)methanone in analogy to example 1a to give the title compound (65%) as a yellow solid. MS (m/z)=414.2 [(M+H)$^+$].

Example 32

5-(3,3-Dimethyl-6-(2-methylpyrimidin-5-yl)-2-oxoindolin-1-yl)-N-(2,2,2-trifluoroethyl)nicotinamide

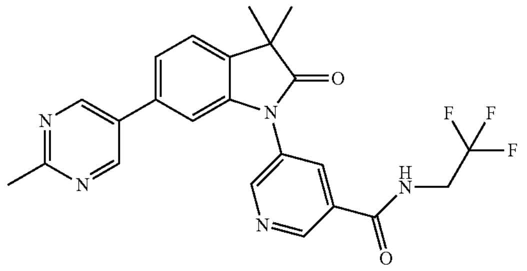 [SMILES: Cc1ncc(-c2ccc3c(c2)N(c2cncc(C(=O)NCC(F)(F)F)c2)C(=O)C3(C)C)cn1]

a) 5-Bromo-N-(2,2,2-trifluoroethyl)nicotinamide

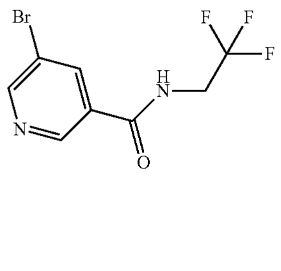 [SMILES: O=C(NCC(F)(F)F)c1cncc(Br)c1]

Example 32a was prepared from 5-bromonicotinic acid with 2,2,2-trifluorethylamine in analogy to example 19a to give the title compound (50%) as a light yellow solid.

MS (m/z)=285.0 [(M+H)$^+$].

b) 5-(3,3-Dimethyl-6-(2-methylpyrimidin-5-yl)-2-oxoindolin-1-yl)-N-(2,2,2-trifluoroethyl)nicotinamide

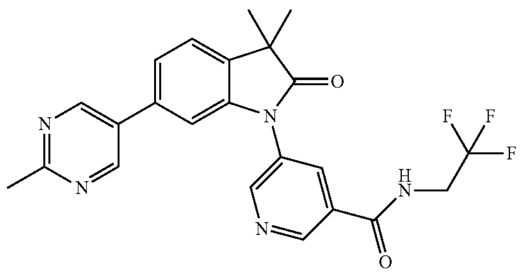 [SMILES: Cc1ncc(-c2ccc3c(c2)N(c2cncc(C(=O)NCC(F)(F)F)c2)C(=O)C3(C)C)cn1]

Example 32b was prepared from 3,3-dimethyl-6-(2-methylpyrimidin-5-yl)indolin-2-one (from WO2014/202493 A1) with 5-bromo-N-(2,2,2-trifluoroethyl)nicotinamide in analogy to example 1a to give the title compound (13%) as a yellow solid. MS (m/z)=456.3 [(M+H)$^+$].

Example 33

5-(3,3-Dimethyl-6-(2-methylpyrimidin-5-yl)-2-oxoindolin-1-yl)-N-methylnicotinamide

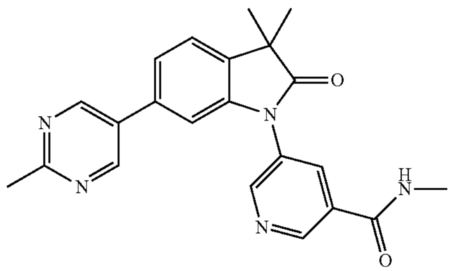

a) 5-Bromo-N-methylnicotinamide

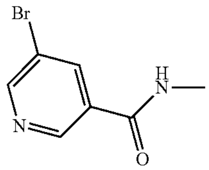

Example 33a was prepared from 5-bromonicotinic acid with methylamine hydrochloride in analogy to example 19a to give the title compound (95%) as a yellow solid.

MS (m/z)=214.9 [(M+H)$^+$].

b) 5-(3,3-Dimethyl-6-(2-methylpyrimidin-5-yl)-2-oxoindolin-1-yl)-N-methylnicotinamide

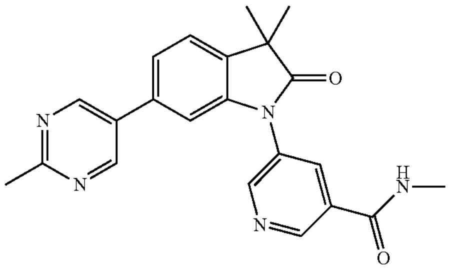

Example 33b was prepared from 3,3-dimethyl-6-(2-methylpyrimidin-5-yl)indolin-2-one (from WO2014/202493 A1) with 5-bromo-N-methylnicotinamide in analogy to example 1a to give the title compound (78%) as a white solid. MS (m/z)=388.2 [(M+H)$^+$].

Example 34

4-(3,3-Dimethyl-6-(2-methylpyrimidin-5-yl)-2-oxoindolin-1-yl)-N,6-dimethylpicolinamide

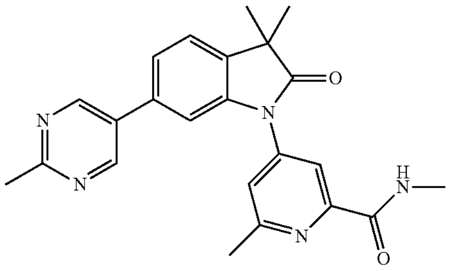

a) 4-Chloro-N,6-dimethylpicolinamide

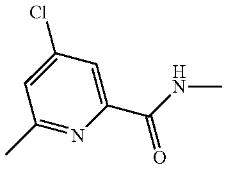

Example 34a was prepared from 4-chloro-6-methylpicolinic acid with methanamine hydrochloride in analogy to example 16a to give the title compound (40%) as a white solid. MS (m/z)=185.0 [(M+H)$^+$].

b) 4-(3,3-Dimethyl-6-(2-methylpyrimidin-5-yl)-2-oxoindolin-1-yl)-N,6-dimethylpicolinamide

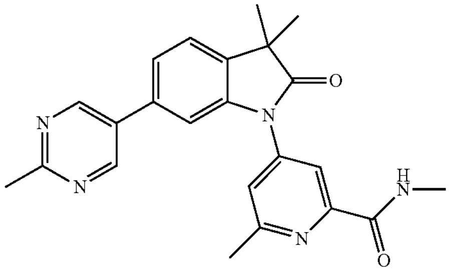

Example 34b was prepared from 3,3-dimethyl-6-(2-methylpyrimidin-5-yl)indolin-2-one (from WO2014/202493 A1) with 4-chloro-N,6-dimethylpicolinamide in analogy to example 22 to give the title compound (84%) as a light yellow solid. MS (m/z)=402.3 [(M+H)$^+$].

Example 35

4-(3,3-Dimethyl-6-(2-methylpyrimidin-5-yl)-2-oxoindolin-1-yl)-N-methylpicolinamide

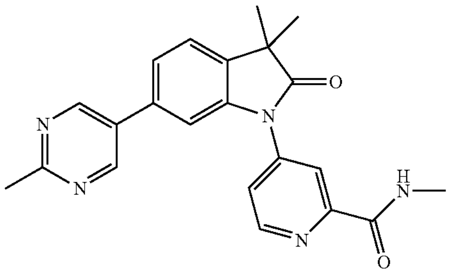

Example 35 was prepared from 3,3-dimethyl-6-(2-methylpyrimidin-5-yl)indolin-2-one (from WO2014/202493 A1) with 4-chloro-N-methylpicolinamide in analogy to example 16b to give the title compound (25%) as a white solid. MS (m/z)=388.2 [(M+H)$^+$].

Example 36

3-(3,3-Dimethyl-6-(2-methylpyrimidin-5-yl)-2-oxoindolin-1-yl)-6-methyl-6,7-dihydro-5H-pyrrolo[3,4-b]pyridin-5-one

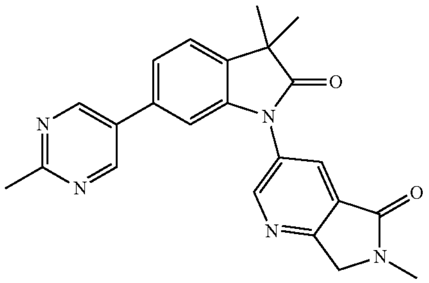

a) Ethyl 5-bromo-2-(bromomethyl)nicotinate

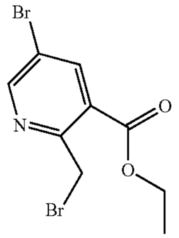

Ethyl 5-bromo-2-methylnicotinate (400 mg, 1.64 mmol, Eq: 1), N-bromosuccinimide (417 mg, 2.29 mmol, Eq: 1.4) and benzoyl peroxide (15.9 mg, 49.2 μmol, Eq: 0.03) were combined with carbon tetrachloride (5 ml). The reaction mixture was heated to 80° C. and stirred for 20 h. The reaction was cooled to 23° C., diluted with 30 ml of ethyl acetate, washed with water and sodium thiosulfate. The organic layers were dried over sodium sulfate and concentrated in vacuo to afford the desired compound as a solid (520 mg, 98%) without further purification.

b) 3-Bromo-6-methyl-6,7-dihydro-5H-pyrrolo[3,4-b]pyridin-5-one

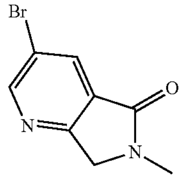

Ethyl 5-bromo-2-(bromomethyl)nicotinate (520 mg, 1.61 mmol, Eq: 1) and methylamin (8.05 ml, 16.1 mmol, Eq: 10) were combined with methanol (3.25 ml). The reaction mixture was stirred for 20 h. The crude reaction mixture was concentrated in vacuo.

The residue was purified by chromatography on silica gel to afford the desired product as a white solid (120 mg, 32%). MS (m/z)=227.1 [M+H]+.

c) 3-(3,3-Dimethyl-6-(2-methylpyrimidin-5-yl)-2-oxoindolin-1-yl)-6-methyl-6,7-dihydro-5H-pyrrolo[3,4-b]pyridin-5-one

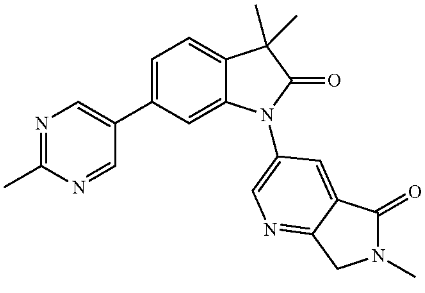

3,3-Dimethyl-6-(2-methylpyrimidin-5-yl)indolin-2-one (100 mg, 395 μmol, Eq: 1, WO2014/202493 A1), 3-bromo-6-methyl-6,7-dihydro-5H-pyrrolo[3,4-b]pyridin-5-one (117 mg, 513 μmol, Eq: 1.30), copper (I) iodide (7.52 mg, 39.5 μmol, Eq: 0.10), potassium carbonate (109 mg, 790 μmol, Eq: 2.00) and trans-N,N-dimethylcyclohexane 1,2-diamine (11.6 mg, 12.8 μl, 79 Eq: 0.20) were combined with degassed 1,4-dioxane (1.2 ml) under argon atmosphere. The reaction mixture was heated to 110° C. and stirred for 20 h. The reaction mixture was poured into saturated sodium bicarbonate and extracted with ethyl acetate (2×). The organic layers were combined and washed with water and brine. The organic phase was dried over sodium sulfate then filtered and concentrated in vacuo.

The residue was purified by chromatography on silica gel to afford the desired product as a yellow solid (100 mg, 63%). MS (m/z)=400.3 [M+H]+.

Example 37

3,3-Dimethyl-1-(2-methyl-3-oxoisoindolin-5-yl)-6-(2-methylpyrimidin-5-yl)indolin-2-one

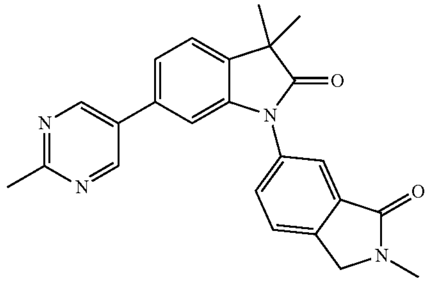

Example 37 was prepared from 3,3-dimethyl-6-(2-methylpyrimidin-5-yl)indolin-2-one (from WO2014/202493 A1) with 6-bromo-2-methylisoindolin-1-one in analogy to example 36 to give the title compound (44%) as an off-white solid. MS (m/z)=399.3 [(M+H)$^+$].

Example 38

2-(3,3-Dimethyl-6-(2-methylpyrimidin-5-yl)-2-oxoindolin-1-yl)-5,5-dimethyl-5H-pyrrolo[3,4-b]pyridin-7(6H)-one

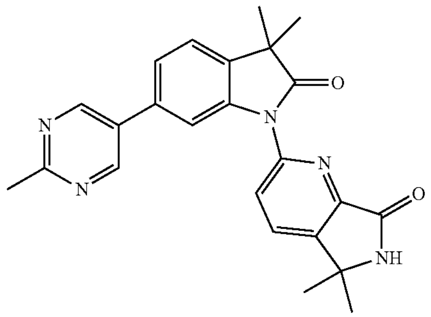 [SMILES: Cc1ncc(-c2ccc3c(c2)N(c2ccc4c(n2)C(=O)NC4(C)C)C(=O)C3(C)C)cn1]

a) Methyl 3-(bromomethyl)-6-chloropicolinate

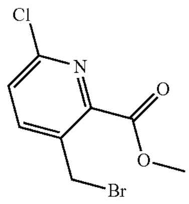

Methyl 6-chloro-3-methylpicolinate (100 mg, 539 μmol, Eq: 1) and N-bromosuccinimide (95.9 mg, 539 μmol, Eq: 1) were dissolved in 1,2-dichloroethane (1.1 ml) under argon atmosphere. Azobisisobutyronitrile (8.85 mg, 53.9 μmol, Eq: 0.1) was then added. The reaction mixture was stirred at 85° C. for 3 days, after 2 more additions of N-bromosuccinimide and azobisisobutyronitrile. The reaction mixture was concentrated in vacuo.

The residue was purified by chromatography on silica gel to afford the desired product as a white solid (92 mg, 64%). MS (m/z)=266.0 [M+H]+.

b) 2-Chloro-6-(4-methoxybenzyl)-5H-pyrrolo[3,4-b]pyridin-7(6H)-one

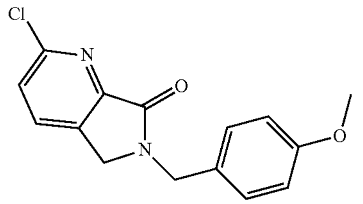 [SMILES: COc1ccc(CN2Cc3ccc(Cl)nc3C2=O)cc1]

Methyl 3-(bromomethyl)-6-chloropicolinate (92 mg, 348 μmol, Eq: 1) was dissolved in tetrahydrofuran (1.39 ml). (4-Methoxyphenyl)methanamine (57.3 mg, 54.5 μl, 417 μmol, Eq: 1.2) and N,N-diisopropylethylamine (89.9 mg, 121 μl, 696 μmol, Eq: 2) were added. The reaction was stirred at room temperature overnight. The reaction mixture was concentrated in vacuo.

The residue was purified by chromatography on silica gel to afford the desired product as a white solid (69 mg, 69%). MS (m/z)=289.2 [M+H]+.

c) 2-Chloro-6-(4-methoxybenzyl)-5,5-dimethyl-5H-pyrrolo[3,4-b]pyridin-7(6H)-one

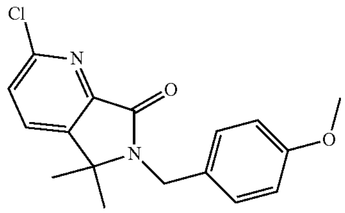 [SMILES: COc1ccc(CN2C(=O)c3nc(Cl)ccc3C2(C)C)cc1]

2-Chloro-6-(4-methoxybenzyl)-5H-pyrrolo[3,4-b]pyridin-7(6H)-one (70 mg, 242 μmol, Eq: 1) was combined with tetrahydrofuran (1.21 ml). Sodium hydride (29.1 mg, 727 μmol, Eq: 3) was slowly added at 0° C. The reaction mixture was stirred at 0° C. for 30 min. Then methyl iodide (172 mg, 75.8 μl, 1.21 mmol, Eq: 5) was added at 0° C. The mixture was stirred at room temperature for 1 h. The reaction mixture was poured into 25 ml of water and extracted with ethyl acetate (2×25 mL). The organic layers were washed with water, dried over sodium sulfate and concentrated in vacuo.

The residue was purified by chromatography on silica gel to afford the desired product as a white solid (48 mg, 62%). MS (m/z)=317.2 [M+H]+.

d) 2-(3,3-Dimethyl-6-(2-methylpyrimidin-5-yl)-2-oxoindolin-1-yl)-6-(4-methoxybenzyl)-5,5-dimethyl-5H-pyrrolo[3,4-b]pyridin-7(6H)-one

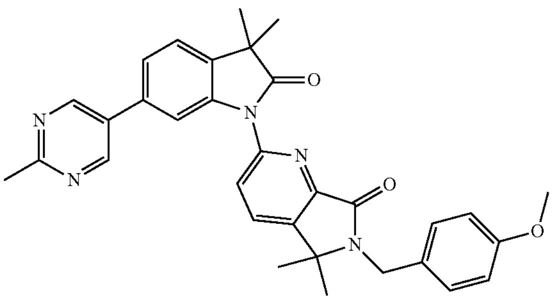

A suspension of 3,3-dimethyl-6-(2-methylpyrimidin-5-yl)indolin-2-one (0.035 g, 138 μmol, Eq: 1, WO2014/202493 A1), 2-chloro-6-(4-methoxybenzyl)-5,5-dimethyl-5H-pyrrolo[3,4-b]pyridin-7(6H)-one (48.1 mg, 152 μmol, Eq: 1.1) and cesium carbonate (58.5 mg, 180 μmol, Eq: 1.3) in dioxane (1.38 ml) was sparged with argon for 5 minutes. Then xantphos (16 mg, 27.6 μmol, Eq: 0.2) and tris(dibenzylideneacetone)dipalladium(0) (25.3 mg, 27.6 μmol, Eq: 0.2) were added, the tube was sealed and the reaction heated to 120° C. for 24 h. The crude mixture was concentrated in vacuo.

The residue was purified by chromatography on silica gel to afford the desired product as a light brown amorphous solid (64 mg, 86%). MS (m/z)=414.3 [M+H]+.

e) 2-(3,3-Dimethyl-6-(2-methylpyrimidin-5-yl)-2-oxoindolin-1-yl)-5,5-dimethyl-5H-pyrrolo[3,4-b]pyridin-7(6H)-one

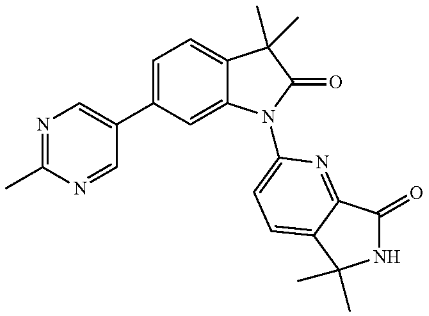 [SMILES: Cc1ncc(-c2ccc3c(c2)N(c2ccc4c(n2)C(=O)NC4(C)C)C(=O)C3(C)C)cn1]

A solution of 2-(3,3-dimethyl-6-(2-methylpyrimidin-5-yl)-2-oxoindolin-1-yl)-6-(4-methoxybenzyl)-5,5-dimethyl-5H-pyrrolo[3,4-b]pyridin-7(6H)-one (0.057 g, 107 μmol, Eq: 1) in trifluoroacetic acid (731 mg, 494 μl, 6.41 mmol, Eq: 60) was heated from 110° C. to 125° C. in a sealed tube for 3 days. The reaction mixture was diluted with ethyl acetate and water and basified with 1M aqueous sodium carbonate solution. The mixture was extracted 2 times with ethyl acetate and the organic layers were washed with 1M aqueous sodium carbonate solution. The combined organic layers were dried with sodium sulfate, filtered and concentrated in vacuo. The residue was purified by chromatography on silica gel to afford the desired product as a brown solid (20 mg, 45%). MS (m/z)=414.3 [M+H]+.

Example 39

N-Cyclopropyl-6-(3,3-dimethyl-6-(2-methylpyrimidin-5-yl)-2-oxoindolin-1-yl)pyrazine-2-carboxamide

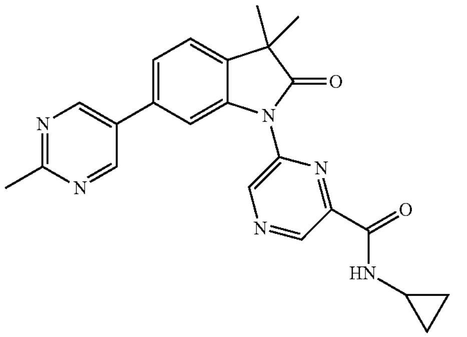 [SMILES: Cc1ncc(-c2ccc3c(c2)N(c2cncc(C(=O)NC4CC4)n2)C(=O)C3(C)C)cn1]

Example 39 was prepared from 1-(6-chloropyrazin-2-yl)-3,3-dimethyl-6-(2-methylpyrimidin-5-yl)indolin-2-one (Example 2a) with cyclopropanamine in analogy to example 3 to give the title compound (53%) as a white solid. MS (m/z)=515.3 [(M+H)$^+$].

Example 40

N-(3,3-Difluorocyclobutyl)-6-(3,3-dimethyl-6-(2-methylpyrimidin-5-yl)-2-oxoindolin-1-yl)pyrazine-2-carboxamide

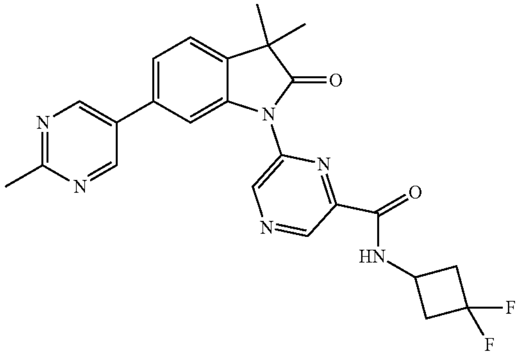 [SMILES: Cc1ncc(-c2ccc3c(c2)N(c2cncc(C(=O)NC4CC(F)(F)C4)n2)C(=O)C3(C)C)cn1]

Example 40 was prepared from 1-(6-chloropyrazin-2-yl)-3,3-dimethyl-6-(2-methylpyrimidin-5-yl)indolin-2-one (Example 2a) with 3,3-difluorocyclobutan amine hydrochloride in analogy to example 2b to give the title compound (41%) as a light grey solid. MS (m/z)=465.3 [(M+H)$^+$].

Example 41

5-(3,3-Dimethyl-6-(2-methylpyrimidin-5-yl)-2-oxoindolin-1-yl)-N,2-dimethylnicotinamide

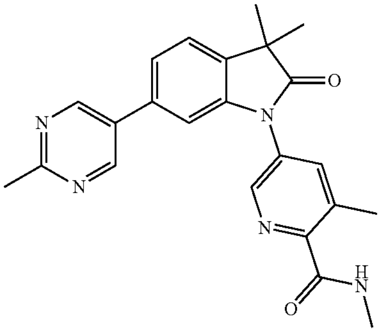

a) Methyl 5-bromo-3-(bromomethyl)picolinate

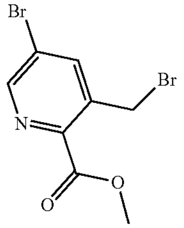

Methyl 5-bromo-3-methylpicolinate (600 mg, 2.61 mmol, Eq: 1), N-bromosuccinimide (663 mg, 3.65 mmol, Eq: 1.4) and benzoyl peroxide (25.3 mg, 78.2 μmol, Eq: 0.03) were combined with carbon tetrachloride (7.5 ml). The reaction mixture was heated to 80° C. and stirred for 20 h. The reaction was cooled to 23° C., diluted with 30 ml of ethyl acetate, washed with water and sodium thiosulfate. The organic layers were dried over sodium sulfate and concentrated in vacuo to give the desired compound as a white solid (800 mg, 99%). MS (m/z)=310.0 [M+H]+.

b) 5-Bromo-N,3-dimethylpicolinamide

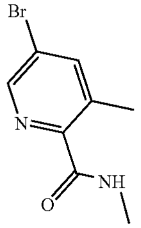

Methyl 5-bromo-3-(bromomethyl)picolinate (800 mg, 2.59 mmol, Eq: 1) and a methylamine solution (12.9 ml, 25.9 mmol, Eq: 10) were combined with methanol (5 ml). The reaction mixture was stirred for 20 h. The crude reaction mixture was concentrated in vacuo. The residue was purified by chromatography on silica gel to afford the desired product as a light yellow solid (59 mg, 10%). MS (m/z)=229.0 [M+H]+.

c) 5-[3,3-Dimethyl-6-(2-methylpyrimidin-5-yl)-2-oxo-indolin-1-yl]-N,3-dimethyl-pyridine-2-carboxamide

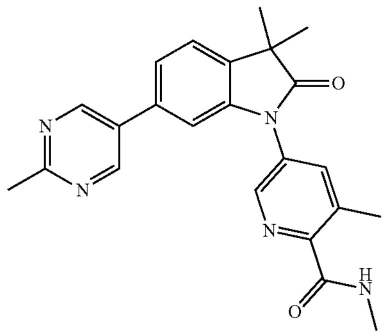

Example 41c was prepared from 3,3-dimethyl-6-(2-methylpyrimidin-5-yl)indolin-2-one (from WO2014/202493 A1) with 5-bromo-N,3-dimethylpicolinamide in analogy to example 36 to give the title compound (64%) as a white solid. MS (m/z)=402.3 [(M+H)$^+$].

Example 42

N-Cyclobutyl-6-(3,3-dimethyl-6-(2-methylpyrimidin-5-yl)-2-oxoindolin-1-yl)pyrazine-2-carboxamide

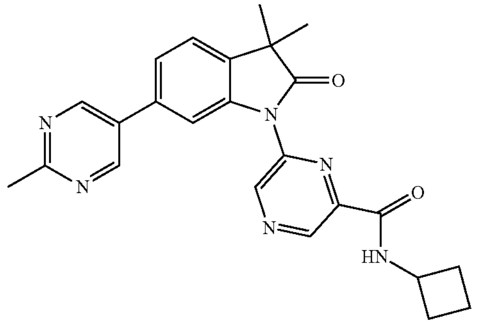 [SMILES: Cc1ncc(-c2ccc3c(c2)N(c2cncc(C(=O)NC4CCC4)n2)C(=O)C3(C)C)cn1]

Example 42 was prepared from 1-(6-chloropyrazin-2-yl)-3,3-dimethyl-6-(2-methylpyrimidin-5-yl)indolin-2-one (Example 2a) with cyclobutylamine in analogy to example 2b to give the title compound (51%) as a light yellow solid. MS (m/z)=429.3 [(M+H)$^+$].

Example 43

6-(3,3-Dimethyl-6-(2-methylpyrimidin-5-yl)-2-oxoindolin-1-yl)-N-(oxetan-3-yl)pyrazine-2-carboxamide

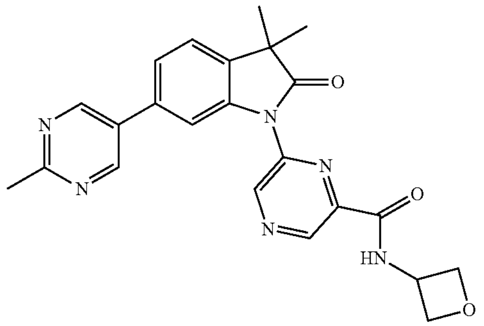 [SMILES: Cc1ncc(-c2ccc3c(c2)N(c2cncc(C(=O)NC4COC4)n2)C(=O)C3(C)C)cn1]

Example 43 was prepared from 1-(6-chloropyrazin-2-yl)-3,3-dimethyl-6-(2-methylpyrimidin-5-yl)indolin-2-one (Example 2a) with 3-oxetanamine in analogy to example 2b to give the title compound (46%) as a white solid. MS (m/z)=431.3 [(M+H)$^+$].

Example 44

N-(tert-Butyl)-6-(3,3-dimethyl-6-(2-methylpyrimidin-5-yl)-2-oxoindolin-1-yl)pyrazine-2-carboxamide

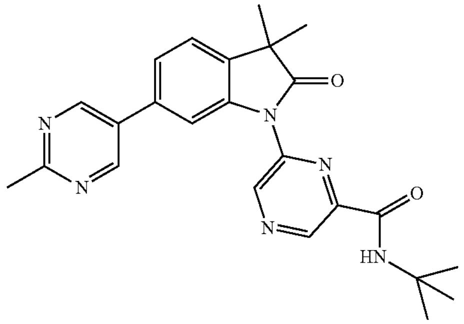 [SMILES: Cc1ncc(-c2ccc3c(c2)N(c2cncc(C(=O)NC(C)(C)C)n2)C(=O)C3(C)C)cn1]

Example 44 was prepared from 1-(6-chloropyrazin-2-yl)-3,3-dimethyl-6-(2-methylpyrimidin-5-yl)indolin-2-one (Example 2a) with tert-butylamine in analogy to example 2b to give the title compound (55%) as a yellow solid. MS (m/z)=431.4 [(M+H)$^+$].

Example 45

4-(3,3-Dimethyl-6-(2-methylpyrimidin-5-yl)-2-oxoindolin-1-yl)-N,1-dimethyl-1H-imidazole-2-carboxamide

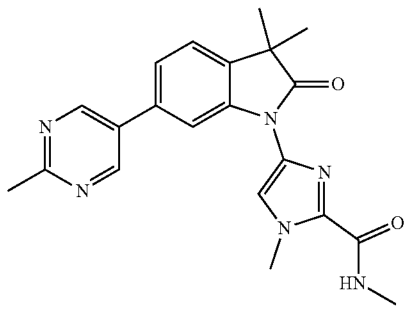 [SMILES: CNC(=O)c1nc(N2C(=O)C(C)(C)c3ccc(-c4cnc(C)nc4)cc32)cn1C]

a) 1-(4-Bromo-1-methyl-1H-imidazol-2-yl)-2,2,2-trichloroethanone

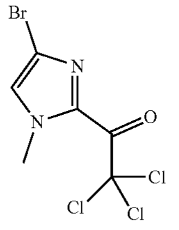

To a solution of 2,2,2-trichloro-1-(1-methyl-1H-imidazol-2-yl)ethanone (0.98 g, 4.31 mmol, Eq: 1) in dry tetrahydrofuran (17.2 ml) was added N-bromosuccinimide (1.53 g, 8.62 mmol, Eq: 2) at −15° C. It was then stirred at room temperature for 20 h and the mixture was concentrated in vacuo.

The residue was purified by chromatography on silica gel to afford the desired product as a light yellow solid (331 mg, 25%).

b) Methyl 4-bromo-1-methyl-1H-imidazole-2-carboxylate

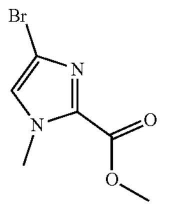

A suspension of 1-(4-bromo-1-methyl-1H-imidazol-2-yl)-2,2,2-trichloroethanone (0.266 g, 868 Eq: 1) in methanol (1.11 g, 1.41 ml, 34.7 mmol, Eq: 40) was heated to reflux for 3 hours then at room temperature overnight. To the reaction mixture, sodium methoxide (15.6 mg, 16.1 μl, 86.8 μmol, Eq: 0.1) was added and stirring was continued at room temperature for 3 hours. The reaction mixture was concentrated in vacuo.

The residue was purified by chromatography on silica gel to afford the desired product as a light brown solid (155 mg, 81%). MS (m/z)=219.1, 221.1 [(M+H)$^+$].

c) 4-Bromo-N,1-dimethyl-1H-imidazole-2-carboxamide

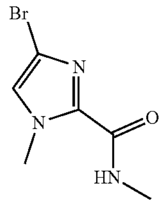

To a suspension of methylamine hydrochloride (78.6 mg, 1.16 mmol, Eq: 3) in dioxane (3.88 ml) was added dropwise 2 M trimethylaluminum in toluene (582 μl, 1.16 mmol, Eq: 3) (slight gas evolution) and the mixture was stirred for 30 minutes at room temperature. Then methyl 4-bromo-1-methyl-1H-imidazole-2-carboxylate (0.085 g, 388 μmol, Eq: 1) was added and the mixture was heated to reflux overnight. The reaction mixture was quenched with 120 ul of water (strong gas evolution) and the mixture was stirred for 15 minutes at room temperature. Then sodium sulfate was added and the stirring was continued for 1 hour. The suspension was filtered and washed with dichloromethane and dichloromethane/methanol 9:1. The obtained solution was concentrated in vacuo.

The residue was purified by chromatography on silica gel to afford the desired product as a white solid (51 mg, 60%). MS (m/z)=218.1, 220.1 [(M+H)$^+$].

d) 4-(3,3-Dimethyl-6-(2-methylpyrimidin-5-yl)-2-oxoindolin-1-yl)-N,1-dimethyl-1H-imidazole-2-carboxamide

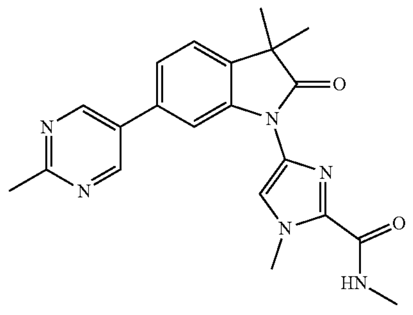 [SMILES: CNC(=O)c1nc(N2C(=O)C(C)(C)c3ccc(-c4cnc(C)nc4)cc32)cn1C]

Example 45d was prepared from 3,3-dimethyl-6-(2-methylpyrimidin-5-yl)indolin-2-one (from WO2014/202493 A1) with 4-bromo-N,1-dimethyl-lll-imidazole-2-carboxamide in analogy to example 23b to give the title compound (73%) as a white solid. MS (m/z)=391.3 [(M+H)$^+$].

Example 46

4-(3,3-Dimethyl-6-(2-methylpyrimidin-5-yl)-2-oxoindolin-1-yl)-N,N,1-trimethyl-1H-imidazole-2-carboxamide

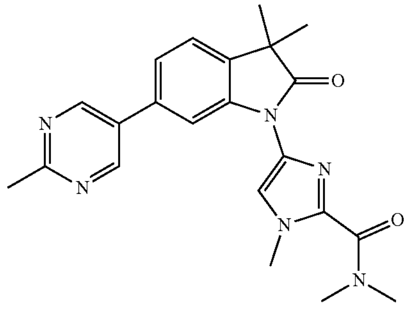 [SMILES: Cc1ncc(-c2ccc3c(c2)N(c2cn(C)c(C(=O)N(C)C)n2)C(=O)C3(C)C)cn1]

a) 4-Bromo-N,N,1-trimethyl-1H-imidazole-2-carboxamide

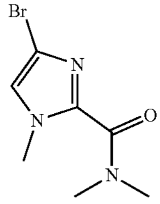

Example 46a was prepared from methyl 4-bromo-1-methyl-1H-imidazole-2-carboxylate (Example 45b) with dimethylamine hydrochloride in analogy to example 45c to give the title compound (22%) as a white solid. MS (m/z) =232.0, 234.0 [(M+H)$^+$].

b) 4-(3,3-Dimethyl-6-(2-methylpyrimidin-5-yl)-2-oxoindolin-1-yl)-N,N,1-trimethyl-1H-imidazole-2-carboxamide

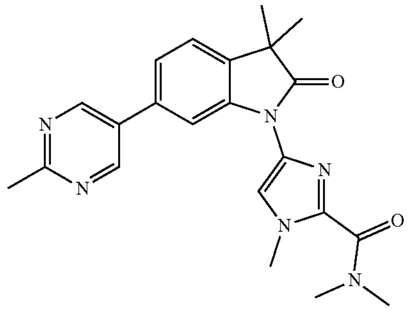 [SMILES: Cc1ncc(-c2ccc3c(c2)N(c2cn(C)c(C(=O)N(C)C)n2)C(=O)C3(C)C)cn1]

Example 46b was prepared from 3,3-dimethyl-6-(2-methylpyrimidin-5-yl)indolin-2-one (from WO2014/202493 A1) with 4-bromo-N,N,1-trimethyl-1H-imidazole-2-carboxamide in analogy to example 23b to give the title compound (84%) as a white solid. MS (m/z)=405.3 [(M+H)$^+$].

Now it has been found that the compounds of formula I may be used for the treatment of CNS diseases.

Biological Assays and Data

The described compounds of formula I reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digiscan Analyzer linked to a computer that constantly collected the beam status information. Records of photocell beam interruptions for individual animals were taken every 5 min over the duration of the experimental session and the sum of the first 6 periods was used as the final parameter. At least 8 mice were used in each treatment group. Compounds were administered i.p. 15 min before a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

((Veh+*L*-687,414 horizontal activity−drug+*L*-687,414 horizontal activity)/Veh+*L*-687,414 horizontal activity)×100

$ID_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney U test (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

Determination of Adenosine Transport Activity

To measure adenosine transport activity of ENT-1 mammalian cells, stable cells expressing the mouse ENT-1 transporter were plated on day 1 in 96-well culture plates at the density of 60,000 cells/well, in complete DMEM/F12 medium supplemented with glutamax, 10% FBS and 10 μg/ml puromycin. On day 2, the medium was aspirated and the cells were washed twice with uptake buffer (10 mM Hepes-Tris, pH 7.4 containing 150 mM NaCl, 1 mM $CaCl_2$, 2.5 mM KCl, 2.5 mM $MgSO_4$, 10 mM D-glucose) (UB). For inhibition experiments, cells were then incubated at RT with various concentrations of compounds with 1% DMSO final. Non-specific uptake was defined in the presence of 10 µM S-(4-Nitrobenzyl)-6-thioinosine (NBTI, Sigma Cat #N2255).

A solution containing [2,8-$^3$H]-adenosine 6 nM (40 Ci/mmol, American Radiolabeled chemicals Inc, Cat #ART 0287A) was then immediately added to the wells. The plates were then incubated for 20 min with gentle shaking and the reaction was stopped by aspiration of the mixture and washing (three times) with ice-cold UB. The cells were lysed by the addition of scintillation liquid, shaken 3 hours and the radioactivity in the cells was estimated using a microplates scintillation counter (TopCount NXT, Packard).

TABLE 1

Effects of compounds of formula I on ENT1 inhibition

| Expl. | structure | Compound of formula | ENT1, adenosine uptake, $IC_{50}$ (uM) |
|---|---|---|---|
| 1 | 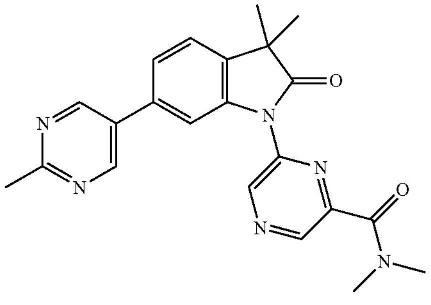 | IA | 0.0195 |
| 2 | 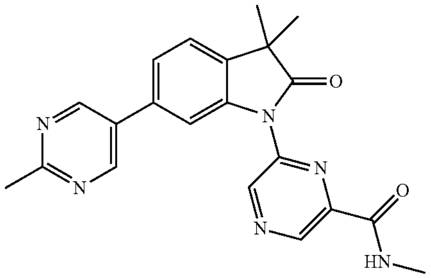 | IA | 0.0280 |
| 3 | 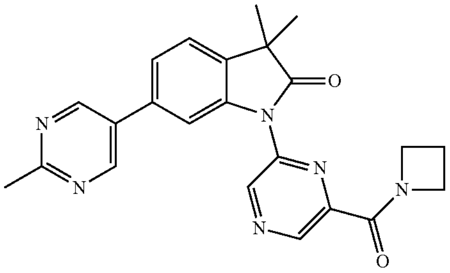 [SMILES: Cc1ncc(-c2ccc3c(c2)N(c2cncc(C(=O)N4CCC4)n2)C(=O)C3(C)C)cn1] | IA | 0.0314 |
| 4 | 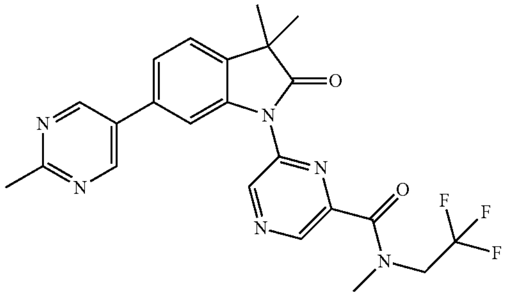 [SMILES: Cc1ncc(-c2ccc3c(c2)N(c2cncc(C(=O)N(C)CC(F)(F)F)n2)C(=O)C3(C)C)cn1] | IA | 0.5127 |

TABLE 1-continued
| Effects of compounds of formula I on ENT1 inhibition | | | |
|---|---|---|---|
| Expl. | structure | Compound of formula | ENT1, adenosine uptake, $IC_{50}$ (uM) |
| 5 | 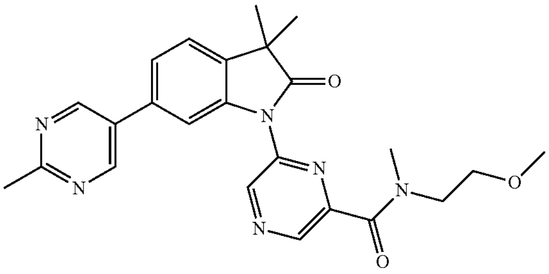 | IA | 0.3823 |
| 6 | 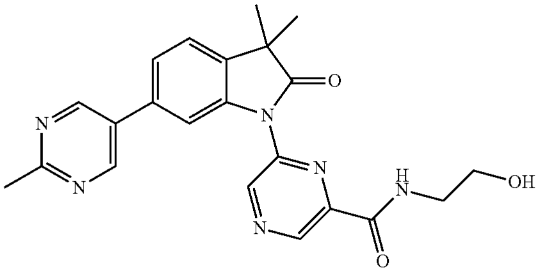 [SMILES: Cc1ncc(-c2ccc3c(c2)N(c2cncc(C(=O)NCCO)n2)C(=O)C3(C)C)cn1] | IA | 0.0300 |
| 7 | 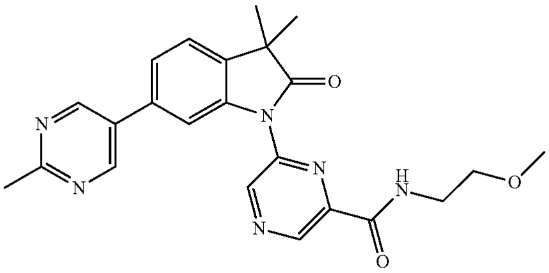 | IA | 0.0884 |
| 8 | 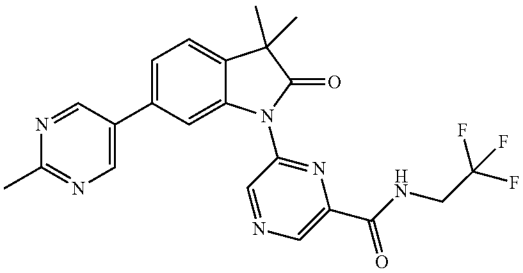 [SMILES: Cc1ncc(-c2ccc3c(c2)N(c2cncc(C(=O)NCC(F)(F)F)n2)C(=O)C3(C)C)cn1] | IA | 0.4511 |
| 9 | 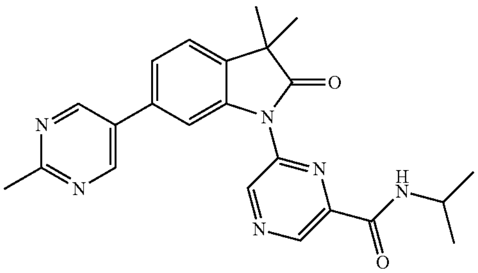 [SMILES: Cc1ncc(-c2ccc3c(c2)N(c2cncc(C(=O)NC(C)C)n2)C(=O)C3(C)C)cn1] | IA | 0.1957 |

TABLE 1-continued
Effects of compounds of formula I on ENT1 inhibition
| Expl. | structure | Compound of formula | ENT1, adenosine uptake, $IC_{50}$ (uM) |
|---|---|---|---|
| 10 | 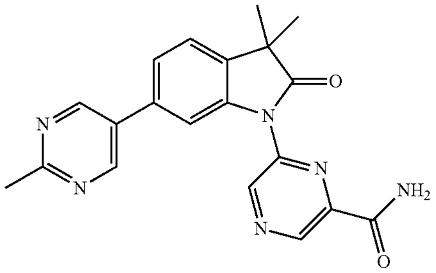 [SMILES: Cc1ncc(-c2ccc3c(c2)N(c2cncc(C(N)=O)n2)C(=O)C3(C)C)cn1] | IA | 0.1969 |
| 11 | 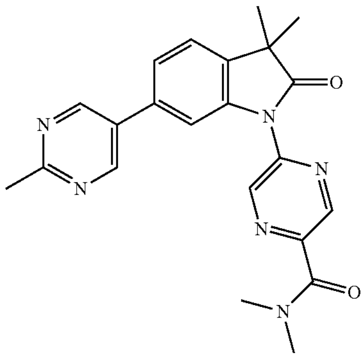 [SMILES: Cc1ncc(-c2ccc3c(c2)N(c2cnc(C(=O)N(C)C)cn2)C(=O)C3(C)C)cn1] | IA | 0.1230 |
| 12 | 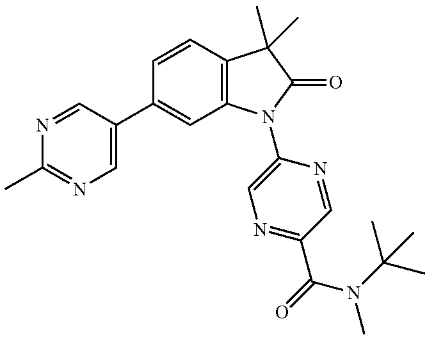 [SMILES: Cc1ncc(-c2ccc3c(c2)N(c2cnc(C(=O)N(C)C(C)(C)C)cn2)C(=O)C3(C)C)cn1] | IA | 0.9268 |
| 13 | 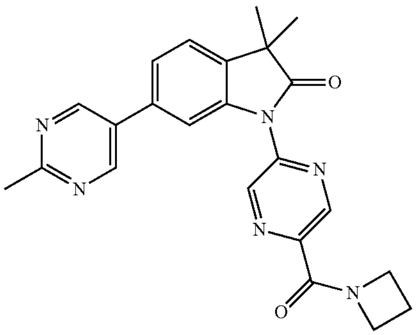 [SMILES: Cc1ncc(-c2ccc3c(c2)N(c2cnc(C(=O)N4CCC4)cn2)C(=O)C3(C)C)cn1] | IA | 0.7665 |

TABLE 1-continued
Effects of compounds of formula I on ENT1 inhibition
| Expl. | structure | Compound of formula | ENT1, adenosine uptake, $IC_{50}$ (uM) |
|---|---|---|---|
| 14 | 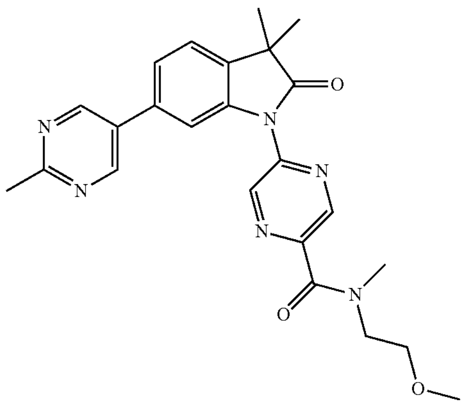 | IA | 0.1860 |
| 15 | 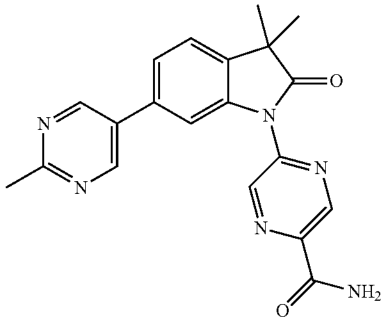 [SMILES: Cc1ncc(-c2ccc3c(c2)N(c2cnc(C(N)=O)cn2)C(=O)C3(C)C)cn1] | IA | 0.3909 |
| 16 | 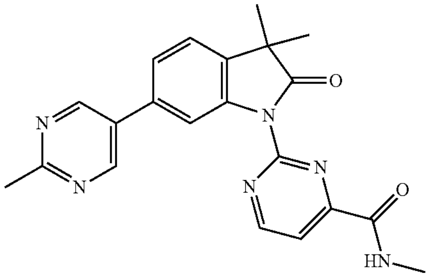 | IB | 0.2410 |
| 17 | 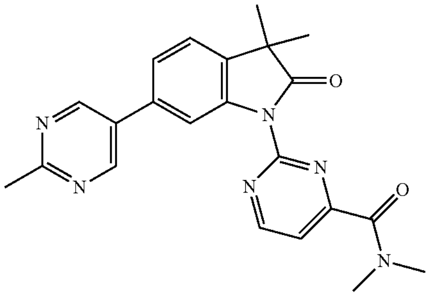 | IB | 0.5366 |

TABLE 1-continued
| Effects of compounds of formula I on ENT1 inhibition | | | |
|---|---|---|---|
| Expl. | structure | Compound of formula | ENT1, adenosine uptake, $IC_{50}$ (uM) |
| 18 | 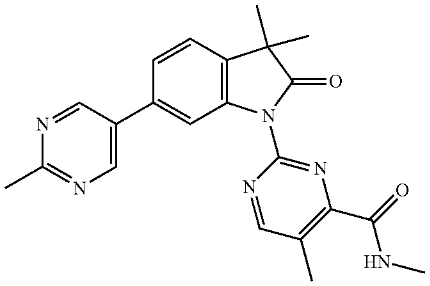 | IB | 0.0784 |
| 19 | 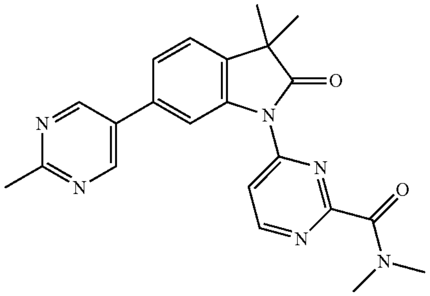 | IC | 0.7251 |
| 20 | 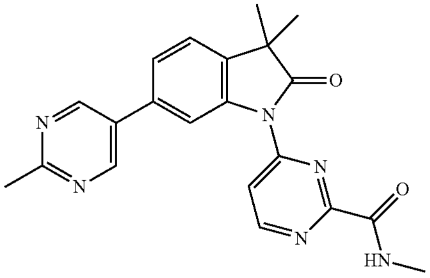 | IC | 0.1203 |
| 21 | 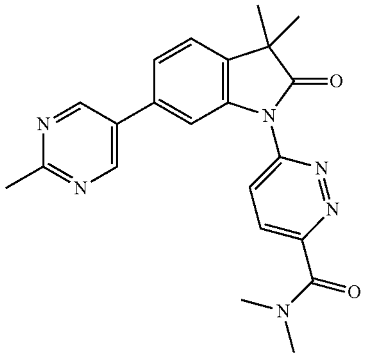 [SMILES: Cc1ncc(-c2ccc3c(c2)N(c2ccc(C(=O)N(C)C)nn2)C(=O)C3(C)C)cn1] | ID | 0.9641 |
| 22 | 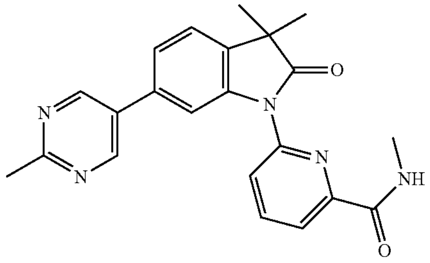 [SMILES: CNC(=O)c1cccc(N2C(=O)C(C)(C)c3ccc(-c4cnc(C)nc4)cc32)n1] | IE | 0.0085 |

TABLE 1-continued
Effects of compounds of formula I on ENT1 inhibition
| Expl. | structure | Compound of formula | ENT1, adenosine uptake, $IC_{50}$ (uM) |
|---|---|---|---|
| 23 | 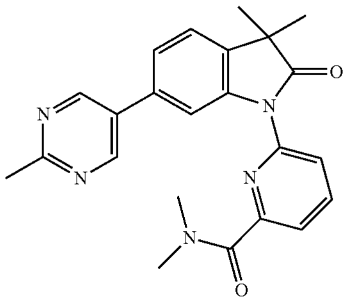 [SMILES: Cc1ncc(-c2ccc3c(c2)N(c2cccc(C(=O)N(C)C)n2)C(=O)C3(C)C)cn1] | IE | 0.3735 |
| 24 | 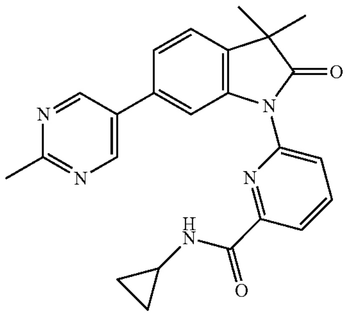 [SMILES: Cc1ncc(-c2ccc3c(c2)N(c2cccc(C(=O)NC4CC4)n2)C(=O)C3(C)C)cn1] | IE | 0.0458 |
| 25 | 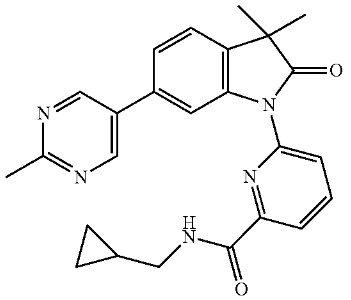 [SMILES: Cc1ncc(-c2ccc3c(c2)N(c2cccc(C(=O)NCC4CC4)n2)C(=O)C3(C)C)cn1] | IE | 0.0499 |
| 26 | 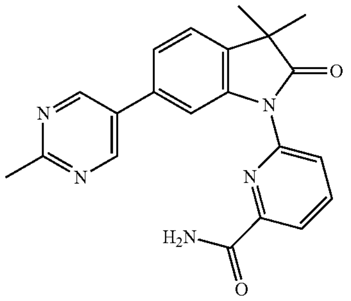 [SMILES: Cc1ncc(-c2ccc3c(c2)N(c2cccc(C(N)=O)n2)C(=O)C3(C)C)cn1] | IE | 0.2526 |
| 27 | 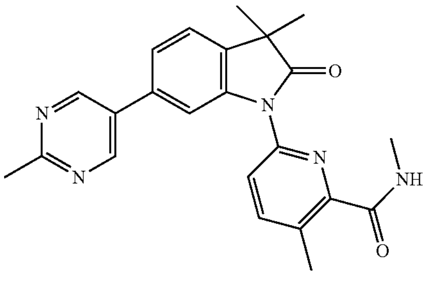 [SMILES: CNC(=O)c1nc(N2C(=O)C(C)(C)c3ccc(-c4cnc(C)nc4)cc32)ccc1C] | IE | 0.0148 |

TABLE 1-continued
| Effects of compounds of formula I on ENT1 inhibition | | | |
|---|---|---|---|
| Expl. | structure | Compound of formula | ENT1, adenosine uptake, $IC_{50}$ (uM) |
| 28 | 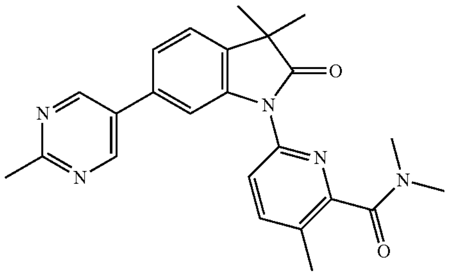 | IE | 0.3507 |
| 29 | 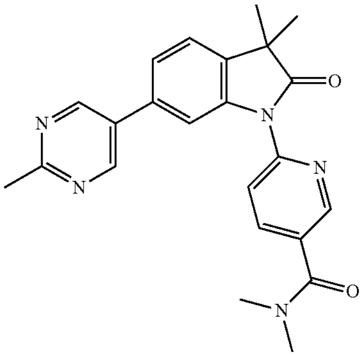 [SMILES: Cc1ncc(-c2ccc3c(c2)N(c2ccc(C(=O)N(C)C)cn2)C(=O)C3(C)C)cn1] | IE | 0.5846 |
| 30 | 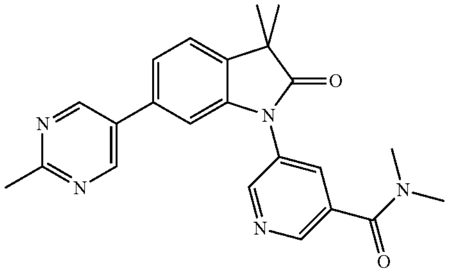 | IF | 0.6083 |
| 31 | 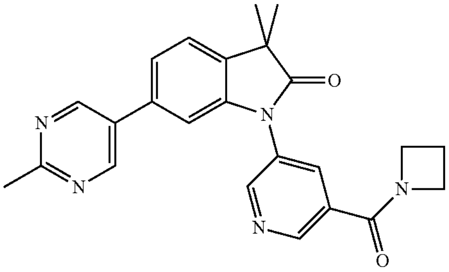 [SMILES: Cc1ncc(-c2ccc3c(c2)N(c2cncc(C(=O)N4CCC4)c2)C(=O)C3(C)C)cn1] | IF | 0.2020 |
| 32 | 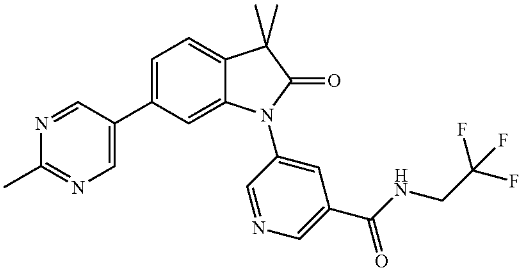 [SMILES: Cc1ncc(-c2ccc3c(c2)N(c2cncc(C(=O)NCC(F)(F)F)c2)C(=O)C3(C)C)cn1] | IF | 0.4773 |

TABLE 1-continued
| Effects of compounds of formula I on ENT1 inhibition | | | |
|---|---|---|---|
| Expl. | structure | Compound of formula | ENT1, adenosine uptake, $IC_{50}$ (uM) |
| 33 | 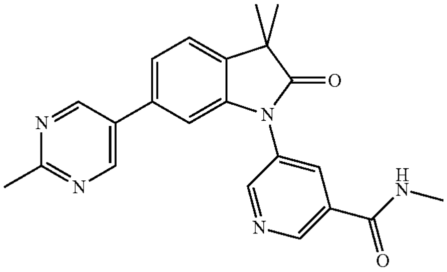 | IF | 0.5588 |
| 34 | 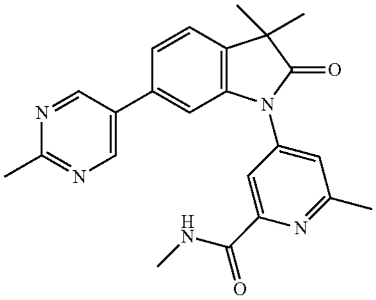 | IG | 1.1400 |
| 35 | 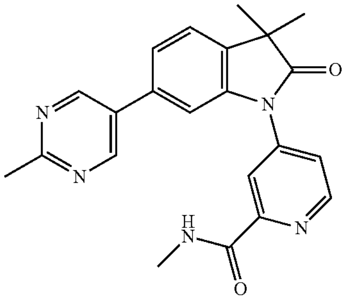 [SMILES: CNC(=O)c1cc(N2C(=O)C(C)(C)c3ccc(-c4cnc(C)nc4)cc32)ccn1] | IG | 0.5337 |
| 36 | 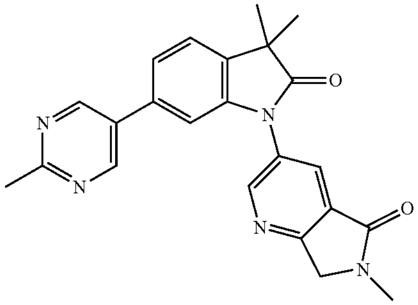 [SMILES: Cc1ncc(-c2ccc3c(c2)N(c2cnc4c(c2)C(=O)N(C)C4)C(=O)C3(C)C)cn1] | Ii-a | 0.6373 |
| 37 | 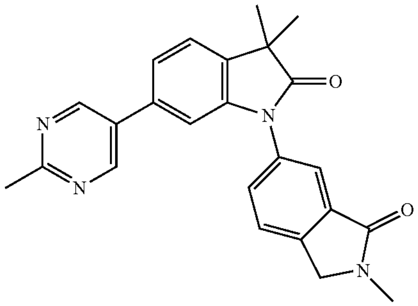 [SMILES: Cc1ncc(-c2ccc3c(c2)N(c2ccc4c(c2)C(=O)N(C)C4)C(=O)C3(C)C)cn1] | Ii-b | 0.6681 |

TABLE 1-continued
| Effects of compounds of formula I on ENT1 inhibition | | | |
|---|---|---|---|
| Expl. | structure | Compound of formula | ENT1, adenosine uptake, $IC_{50}$ (uM) |
| 38 | 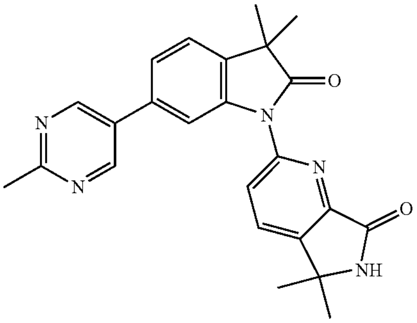 [SMILES: Cc1ncc(-c2ccc3c(c2)N(c2ccc4c(n2)C(=O)NC4(C)C)C(=O)C3(C)C)cn1] | Ii-c | 0.2390 |
| 39 | 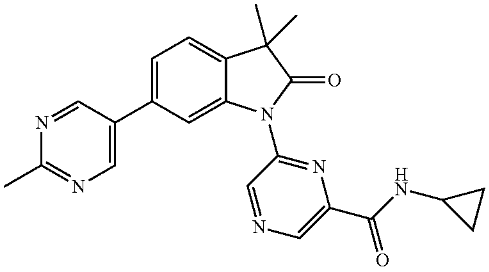 [SMILES: Cc1ncc(-c2ccc3c(c2)N(c2cncc(C(=O)NC4CC4)n2)C(=O)C3(C)C)cn1] | IA | 0.0764 |
| 40 | 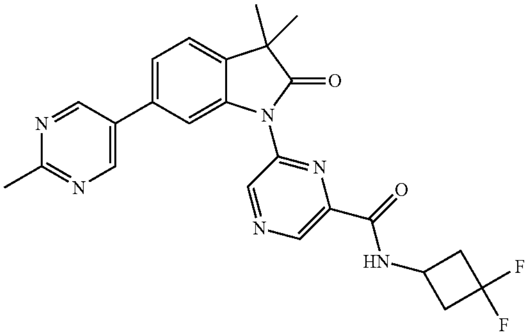 [SMILES: Cc1ncc(-c2ccc3c(c2)N(c2cncc(C(=O)NC4CC(F)(F)C4)n2)C(=O)C3(C)C)cn1] | IA | 0.3234 |
| 41 | 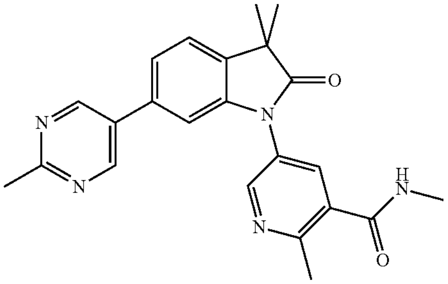 | IF | 0.4132 |

TABLE 1-continued
Effects of compounds of formula I on ENT1 inhibition
| Expl. | structure | Compound of formula | ENT1, adenosine uptake, $IC_{50}$ (uM) |
|---|---|---|---|
| 42 | 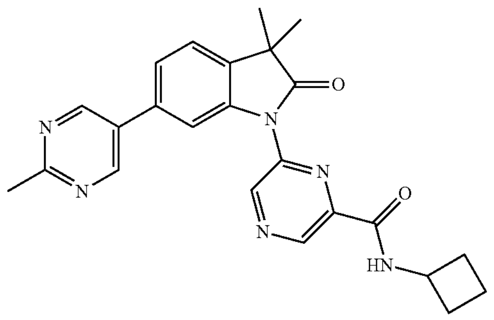 [SMILES: Cc1ncc(-c2ccc3c(c2)N(c2cncc(C(=O)NC4CCC4)n2)C(=O)C3(C)C)cn1] | IA | 0.1286 |
| 43 | 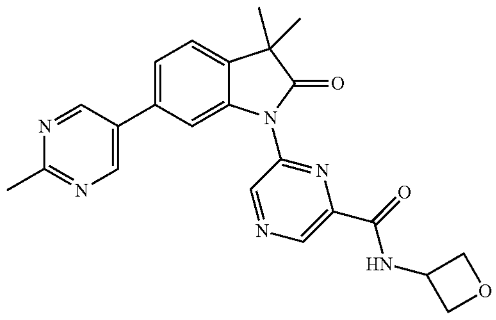 [SMILES: Cc1ncc(-c2ccc3c(c2)N(c2cncc(C(=O)NC4COC4)n2)C(=O)C3(C)C)cn1] | IA | 0.3194 |
| 44 | 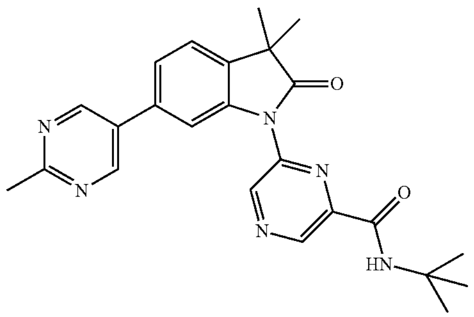 [SMILES: Cc1ncc(-c2ccc3c(c2)N(c2cncc(C(=O)NC(C)(C)C)n2)C(=O)C3(C)C)cn1] | IA | 0.2426 |
| 45 | 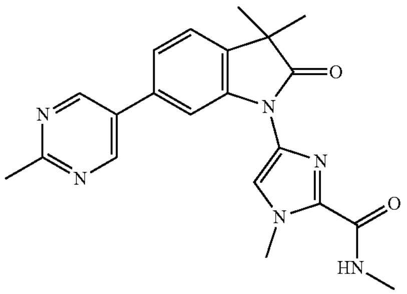 | IH | 0.0210 |

TABLE 1-continued

| Effects of compounds of formula I on ENT1 inhibition | | | |
|---|---|---|---|
| Expl. | structure | Compound of formula | ENT1, adenosine uptake, $IC_{50}$ (uM) |
| 46 | 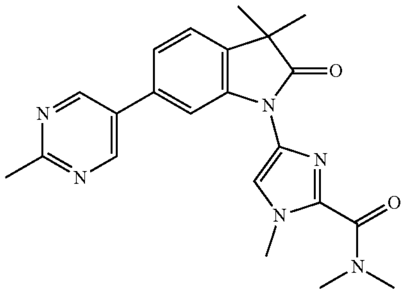 | IH | 0.0469 |

TABLE 2

| Effects of compounds of formula I for reduction of L-687,414-induced hyperlocomotion | | | |
|---|---|---|---|
| | L-687,414-induced hyperlocomotion | | |
| Expl. | Dose ip [mg/kg] | Inhibition, ip [%] | P value |
| 2 | 30 ip | 97.5 | 0.00008 |
| 7 | 30 ip | 88.1 | 0.00008 |
| 11 | 30 ip | 98.4 | 0.00008 |
| 16 | 30 ip | 94.6 | 0.00008 |
| 22 | 30 ip | 95.6 | 0.00008 |
| 24 | 30 ip | 99.1 | 0.00008 |
| 29 | 30 ip | 93 | 0.00008 |

As mentioned above, some compounds have been tested in SmartCube®, an analytical system developed by PsychoGenics Inc.

SmartCube® was used to compare the behavioral signature of a test compound to a database of behavioral signatures obtained from a large set of clinically approved reference drugs, grouped per indications. In this way, the neuropharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each compound and dose (mg/kg), the Y-axis indicates the relative probability that the test compound will show efficacy in the specific CNS indication.

Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies above 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of 0.70.

TABLE 3

| Similarity analysis of compounds of formula I showing effects in SmartCube ® | | | |
|---|---|---|---|
| Example | Clozapine (1.0 mg/kg) | Olanzapine (0.25 mg/kg) | Risperidone (0.06 mg/kg) |
| 2 (3 mg/kg) | 0.54 | 0.51 | 0.63 |
| 7 (3 mg/kg) | 0.57 | 0.61 | 0.59 |
| 11 (3 mg/kg) | 0.57 | 0.57 | 0.64 |
| 16 (3 mg/kg) | 0.56 | 0.54 | 0.52 |
| 24 (3 mg/kg) | 0.61 | 0.69 | 0.65 |
| 29 (5 mg/kg) | 0.60 | 0.67 | 0.63 |

Therefore, it can be assumed that the present compounds have similar efficacies as known atypical antipsychotics.

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The invention claimed is:

1. A compound of formula (I)

I

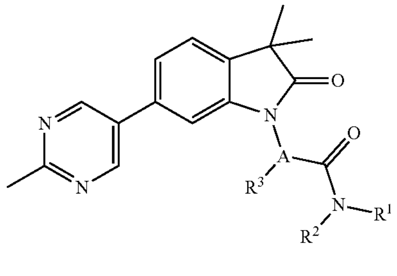

wherein

A is phenyl or a five or six membered heteroaryl group, containing one or two N atoms, selected from

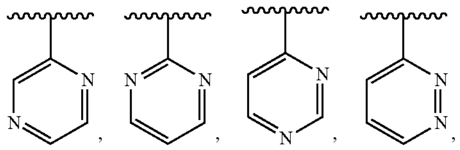

-continued

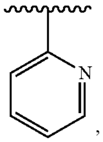, 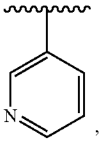, 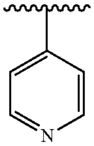, or 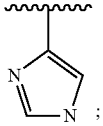;

or the amide group —C(O)—$NR^1R^2$ may form together with two neighboring carbon atoms from the group A an additional fused ring, selected from

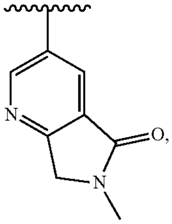, 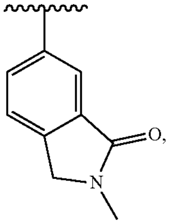, or

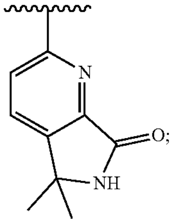;

$R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen;

or $R^1$ and $R^2$ may form together with the N atom to which they are attached the group

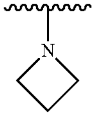;

and $R^3$ is hydrogen or lower alkyl;

or a pharmaceutically acceptable salt thereof.

2. The compound according to claim 1,

IA

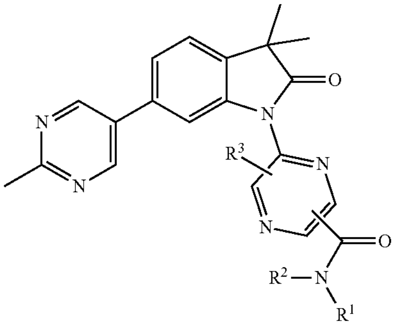

wherein the compound is a compound of Formula IA, wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen;

or $R^1$ and $R^2$ may form together with the N atom to which they are attach the group

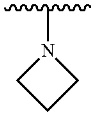;

and $R^3$ is hydrogen or lower alkyl;

or a pharmaceutically acceptable salt thereof.

3. The compound according to claim 2, wherein the compound is:

6-(3,3-dimethyl-6-(2-methylpyrimidin-5-yl)-2-oxoindolin-1-yl)-N,N-dimethylpyrazine-2-carboxamide;

6-(3,3-dimethyl-6-(2-methylpyrimidin-5-yl)-2-oxoindolin-1-yl)-N-methylpyrazine-2-carboxamide;

1-(6-(azetidine-1-carbonyl)pyrazin-2-yl)-3,3-dimethyl-6-(2-methylpyrimidin-5-yl)indolin-2-one;

6-(3,3-dimethyl-6-(2-methylpyrimidin-5-yl)-2-oxoindolin-1-yl)-N-methyl-N-(2,2,2-trifluoroethyl)pyrazine-2-carboxamide;

6-(3,3-dimethyl-6-(2-methylpyrimidin-5-yl)-2-oxoindolin-1-yl)-N-(2-methoxyethyl)-N-methylpyrazine-2-carboxamide;

6-(3,3-dimethyl-6-(2-methylpyrimidin-5-yl)-2-oxoindolin-1-yl)-N-(2-hydroxyethyl)pyrazine-2-carboxamide;

6-(3,3-dimethyl-6-(2-methylpyrimidin-5-yl)-2-oxoindolin-1-yl)-N-(2-methoxyethyl)pyrazine-2-carboxamide;

6-(3,3-dimethyl-6-(2-methylpyrimidin-5-yl)-2-oxoindolin-1-yl)-N-(2,2,2-trifluoroethyl)pyrazine-2-carboxamide;

6-(3,3-dimethyl-6-(2-methylpyrimidin-5-yl)-2-oxoindolin-1-yl)-N-isopropylpyrazine-2-carboxamide;

6-(3,3-dimethyl-6-(2-methylpyrimidin-5-yl)-2-oxoindolin-1-yl)pyrazine-2-carboxamide;

5-[3,3-dimethyl-6-(2-methylpyrimidin-5-yl)-2-oxoindol-1-yl]-dimethylpyrazine-2-carboxamide;

N-(tert-butyl)-5-(3,3-dimethyl-6-(2-methylpyrimidin-5-yl)-2-oxoindolin-1-yl)-N-methylpyrazine-2-carboxamide;

1-(5-(azetidine-1-carbonyl)pyrazin-2-yl)-3,3-dimethyl-6-(2-methylpyrimidin-5-yl)indolin-2-one;

5-(3,3-dimethyl-6-(2-methylpyrimidin-5-yl)-2-oxoindolin-1-yl)-N-(2-methoxyethyl)-N-methylpyrazine-2-carboxamide;

5-(3,3-dimethyl-6-(2-methylpyrimidin-5-yl)-2-oxoindolin-1-yl)pyrazine-2-carboxamide;

N-cyclopropyl-6-(3,3-dimethyl-6-(2-methylpyrimidin-5-yl)-2-oxoindolin-1-yl)pyrazine-2-carboxamide;

N-(3,3-difluorocyclobutyl)-6-(3,3-dimethyl-6-(2-methylpyrimidin-5-yl)-2-oxoindolin-1-yl)pyrazine-2-carboxamide;

N-cyclobutyl-6-(3,3-dimethyl-6-(2-methylpyrimidin-5-yl)-2-oxoindolin-1-yl)pyrazine-2-carboxamide;

6-(3,3-dimethyl-6-(2-methylpyrimidin-5-yl)-2-oxoindolin-1-yl)-N-(oxetan-3-yl)pyrazine-2-carboxamide; or N-(tert-butyl)-6-(3,3-dimethyl-6-(2-methylpyrimidin-5-yl)-2-oxoindolin-1-yl)pyrazine-2-carboxamide, or a pharmaceutically acceptable salt thereof.

4. The compound according to claim 1,

IB

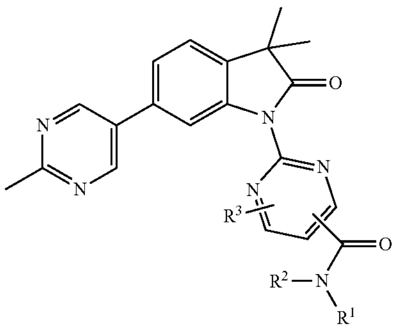

wherein the compound is of Formula (IB), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

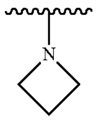

;

and $R^3$ is hydrogen or lower alkyl;

or a pharmaceutically acceptable salt thereof.

5. The compound according to claim 4, wherein the compound is:

2-(3,3-dimethyl-6-(2-methylpyrimidin-5-yl)-2-oxoindolin-1-yl)-N-methylpyrimidine-4-carboxamide;

2-(3,3-dimethyl-6-(2-methylpyrimidin-5-yl)-2-oxoindolin-1-yl)-N,N-dimethylpyrimidine-4-carboxamide; or 2-(3,3-dimethyl-6-(2-methylpyrimidin-5-yl)-2-oxoindolin-1-yl)-N,5-dimethylpyrimidine-4-carboxamide, or a pharmaceutically acceptable salt thereof.

6. The compound according to claim 1,

IC

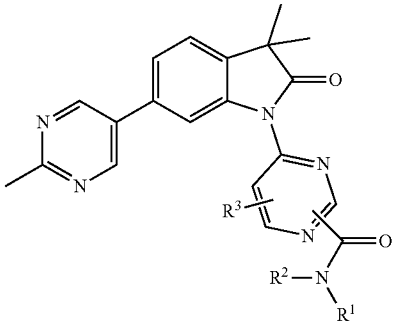

wherein the compound is of Formula (IC), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

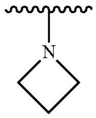

;

and $R^3$ is hydrogen or lower alkyl;

or a pharmaceutically acceptable salt thereof.

7. The compound according to claim 6, wherein the compound is:

4-(3,3-dimethyl-6-(2-methylpyrimidin-5-yl)-2-oxoindolin-1-yl)-N,N-dimethylpyrimidine-2-carboxamide; or 4-(3,3-dimethyl-6-(2-methylpyrimidin-5-yl)-2-oxoindolin-1-yl)-N-methylpyrimidine-2-carboxamide, or a pharmaceutically acceptable salt thereof.

8. The compound according to claim 1,

ID

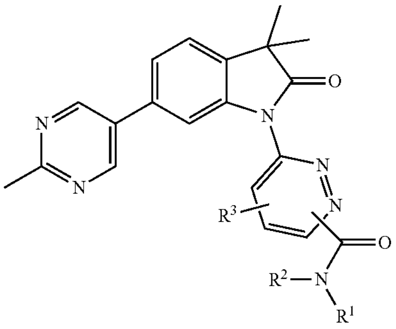

wherein the compound is of Formula (ID), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

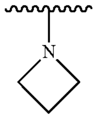

;

and $R^3$ is hydrogen or lower alkyl;

or a pharmaceutically acceptable salt thereof.

9. The compound according to claim 8, wherein the compound is:

6-(3,3-dimethyl-6-(2-methylpyrimidin-5-yl)-2-oxoindolin-1-yl)-N,N-dimethylpyridazine-3-carboxamide, or a pharmaceutically acceptable salt thereof.

10. The compound according to claim 1

IE

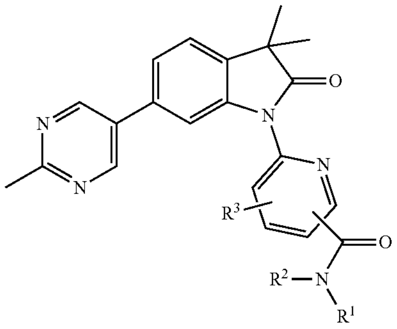

wherein the compound is of Formula (IE), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen;

or $R^1$ and $R^2$ may form together with the N atom to which they are attach the group

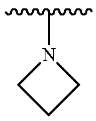
;

and $R^3$ is hydrogen or lower alkyl;

or a pharmaceutically acceptable salt thereof.

11. The compound according to claim 10, wherein the compound is:

6-(3,3-dimethyl-6-(2-methylpyrimidin-5-yl)-2-oxoindolin-1-yl)-N-methylpicolinamide;

6-(3,3-dimethyl-6-(2-methylpyrimidin-5-yl)-2-oxoindolin-1-yl)-N,N-dimethylpicolinamide;

N-cyclopropyl-6-(3,3-dimethyl-6-(2-methylpyrimidin-5-yl)-2-oxoindolin-1-yl)picolinamide;

N-(cyclopropylmethyl)-6-(3,3-dimethyl-6-(2-methylpyrimidin-5-yl)-2-oxoindolin-1-yl)picolinamide;

6-(3,3-dimethyl-6-(2-methylpyrimidin-5-yl)-2-oxoindolin-1-yl)picolinamide;

6-(3,3-dimethyl-6-(2-methylpyrimidin-5-yl)-2-oxoindolin-1-yl)-N,3-dimethylpicolinamide;

6-(3,3-dimethyl-6-(2-methylpyrimidin-5-yl)-2-oxoindolin-1-yl)-N,N,3-trimethylpicolinamide; or 6-(3,3-dimethyl-6-(2-methylpyrimidin-5-yl)-2-oxoindolin-1-yl)-N,N-dimethylnicotinamide, or a pharmaceutically acceptable salt thereof.

12. The compound according to claim 1

IF

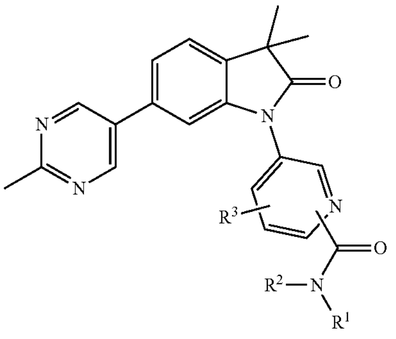

wherein the compound is of Formula (IF), wherein $R^1$ and $R^2$ are independently from each other hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

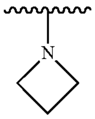
;

and $R^3$ is hydrogen or lower alkyl;

or a pharmaceutically acceptable salt thereof.

13. The compound according to claim 12, wherein the compound is:

5-(3,3-dimethyl-6-(2-methylpyrimidin-5-yl)-2-oxoindolin-1-yl)-N,N-dimethylnicotinamide;

1-(5-(azetidine-1-carbonyl)pyridin-3-yl)-3,3-dimethyl-6-(2-methylpyrimidin-5-yl)indolin-2-one;

5-(3,3-dimethyl-6-(2-methylpyrimidin-5-yl)-2-oxoindolin-1-yl)-N-(2,2,2-trifluoroethyl)nicotinamide;

5-(3,3-dimethyl-6-(2-methylpyrimidin-5-yl)-2-oxoindolin-1-yl)-N-methylnicotinamide; or 5-(3,3-dimethyl-6-(2-methylpyrimidin-5-yl)-2-oxoindolin-1-yl)-N,2-dimethylnicotinamide, or a pharmaceutically acceptable salt thereof.

14. The compound according to claim 1

IG

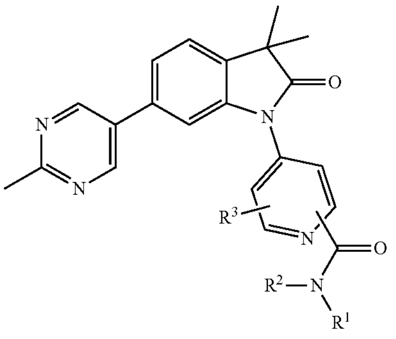

wherein the compound is of Formula (IG), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

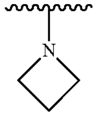 ;

and $R^3$ is hydrogen or lower alkyl;

or a pharmaceutically acceptable salt thereof.

15. The compound according to claim 14, wherein the compound is:

4-(3,3-dimethyl-6-(2-methylpyrimidin-5-yl)-2-oxoindolin-1-yl)-N,6-dimethylpicolinamide; or 4-(3,3-dimethyl-6-(2-methylpyrimidin-5-yl)-2-oxoindolin-1-yl)-N-methylpicolinamide, or a pharmaceutically acceptable salt thereof.

16. The compound according to claim 1

IH

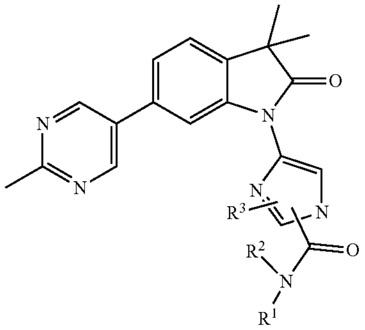

wherein the compound is of Formula (IH), wherein $R^1$ and $R^2$ are independently selected from hydrogen, lower alkyl, lower alkyl substituted by halogen, lower alkyl substituted by hydroxy, —$(CH_2)_2$-lower alkoxy, oxetanyl, cycloalkyl, or $CH_2$-cycloalkyl, which cycloalkyl rings are optionally substituted by halogen; or $R^1$ and $R^2$ may form together with the N atom to which they are attach the group

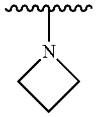 ;

and $R^3$ is hydrogen or lower alkyl;

or a pharmaceutically acceptable salt thereof.

17. The compound according to claim 16, wherein the compound is:

4-(3,3-dimethyl-6-(2-methylpyrimidin-5-yl)-2-oxoindolin-1-yl)-N, 1-dimethyl-1H-imidazole-2-carboxamide; or 4-(3,3-dimethyl-6-(2-methylpyrimidin-5-yl)-2-oxoindolin-1-yl)-N, N, 1-trimethyl-1H-imidazole-2-carboxamide, or a pharmaceutically acceptable salt thereof.

18. The compound according to claim 1, wherein A is phenyl or a five or six membered heteroaryl group, containing one or two N atoms, selected from

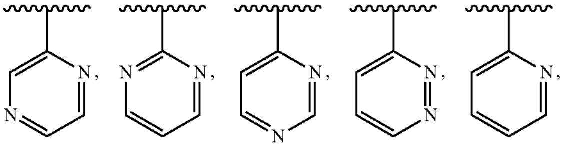

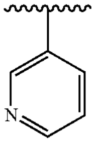, 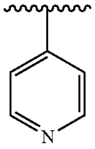 or 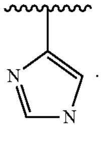.

19. The compound according to claim 1, wherein the compound is:

Ii-a

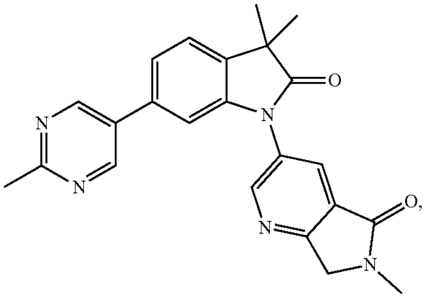,

Ii-b

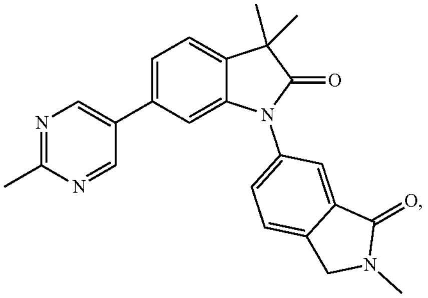,

Ii-c

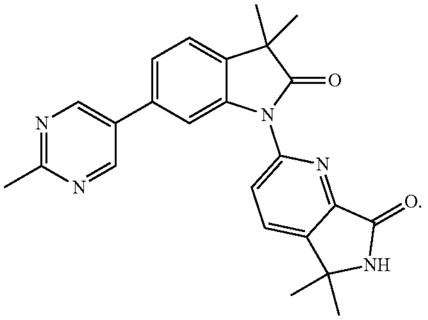.

20. A pharmaceutical composition comprising the compound according to claim 1, or a pharmaceutically acceptable salt thereof, and a pharmaceutically inert, inorganic or organic carrier.

21. A combination of the compound according to claim 1 together with a known marketed antipsychotic, antidepressant, anxiolytic or mood stabilizer.

22. The combination according to claim 21, wherein the known marketed antipsychotic drug is olanzapine, clozapine, risperidone, aripiprazole or ziprasidone.

23. The combination according to claim 21, wherein the known marketed anti-depressive drug is citalopram, escitalopram, paroxetine, fluoxetine, sertraline, duloxetine, milnacipran, venlafaxine, or mirtazapine.

24. The combination according to claim 21, wherein the known marketed anxiolytic drug is alprazolam, chlordiazepoxide, clonazepam, diazepam, Estazolam, eszopiclone, zaleplon, zolpidem, pregabalin or gabapentin.

25. The combination according to claim 21, wherein the known marketed mood stabilizer is carbamazepine, lamotrigine, lithium, or valproic acid.

26. A compound which is 4-(3,3-dimethyl-6-(2-methylpyrimidin-5-yl)-2-oxoindolin-1-yl)-N,1-dimethyl-1H-imidazole-2-carboxamide, or a pharmaceutically acceptable salt thereof.

27. A pharmaceutical composition comprising 4-(3,3-dimethyl-6-(2-methylpyrimidin-5-yl)-2-oxoindolin-1-yl)-N,1-dimethyl-1H-imidazole-2-carboxamide, or a pharmaceutically acceptable salt thereof, and a pharmaceutically inert, inorganic or organic carrier.

28. A compound which is 4-(3,3-dimethyl-6-(2-methylpyrimidin-5-yl)-2-oxoindolin-1-yl)-N,N,1-trimethyl-1H-imidazole-2-carboxamide, or a pharmaceutically acceptable salt thereof.

29. A pharmaceutical composition comprising 4-(3,3-dimethyl-6-(2-methylpyrimidin-5-yl)-2-oxoindolin-1-yl)-N,N, 1-trimethyl-1H-imidazole-2-carboxamide, or a pharmaceutically acceptable salt thereof, and a pharmaceutically inert, inorganic or organic carrier.

30. A compound which is 4-(3,3-dimethyl-6-(2-methylpyrimidin-5-yl)-2-oxoindolin-1-yl)-N,6-dimethylpicolinamide, or a pharmaceutically acceptable salt thereof.

31. A pharmaceutical composition comprising 4-(3,3-dimethyl-6-(2-methylpyrimidin-5-yl)-2-oxoindolin-1-yl)-N, 6-dimethylpicolinamide, or a pharmaceutically acceptable salt thereof, and a pharmaceutically inert, inorganic or organic carrier.

32. A compound which is 4-(3,3-dimethyl-6-(2-methylpyrimidin-5-yl)-2-oxoindolin-1-yl)-N-methylpicolinamide, or a pharmaceutically acceptable salt thereof.

33. A pharmaceutical composition comprising 4-(3,3-dimethyl-6-(2-methylpyrimidin-5-yl)-2-oxoindolin-1-yl)-N-methylpicolinamide, or a pharmaceutically acceptable salt thereof, and a pharmaceutically inert, inorganic or organic carrier.

34. The compound according to claim 1, prepared by reacting a compound of formula (1)

1

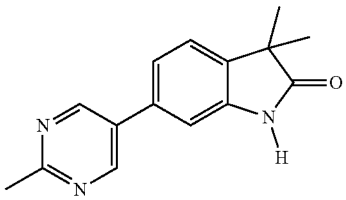

with a compound of formula (2)

$$Y\text{-}A(R^3)\text{—}C(O)\text{—}NR^1R^2 \quad 2$$

to make the compound of formula (I)

I

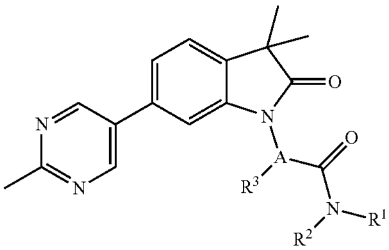

wherein Y is Cl, Br or I and $R^1$, $R^2$ and $R^3$ have the meaning as described in claim 1 and, if desired, converting the compound of formula (I) into a pharmaceutically acceptable salt; or a) reacting a compound of formula (4)

4

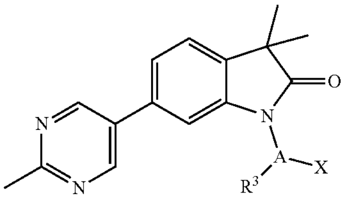

with $HNR^1R^2$ by aminocarbonylation in the presence of a ferrocene-palladium catalyst, with a source of carbon monoxide selected from Molybden-hexacarbonyl or CO gas to make the compound of formula (I)

I

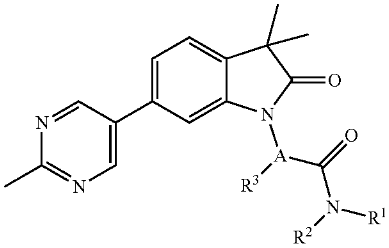

wherein X is Cl or Br and $R^1$, $R^2$ and $R^3$ have the meaning as described in claim 1, and, if desired, converting the compound of formula (I) into a pharmaceutically acceptable salt; or b) amidation of a compound of formula (6)
6
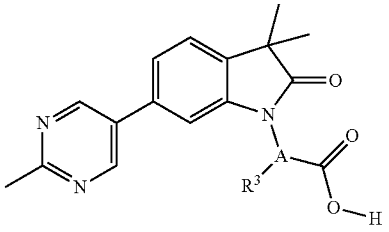
with $HNR^1R^2$
using an activating agent, selected from HATU or TBTU, to give the compound of formula (I)
I
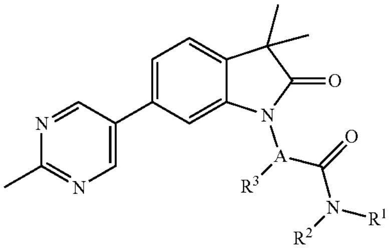
A wherein $R^1$, $R^2$ and $R^3$ have the meaning as described in claim 1, and,
if desired, converting the compound of formula (I) into a pharmaceutically acceptable salt.
* * * * *